(12) United States Patent
Schmaljohn

(10) Patent No.: US 9,675,684 B2
(45) Date of Patent: Jun. 13, 2017

(54) GENE OPTIMIZED HANTAAN VIRUS M SEGMENT DNA VACCINE FOR HEMORRHAGIC FEVER WITH RENAL SYNDROME

(71) Applicant: The United States of America, as represented by the Secretary of the Army, Washington, DC (US)

(72) Inventor: Connie Schmaljohn, Middletown, MD (US)

(73) Assignee: The United States of America as represented by The Secretary of The Army, Washington, DC (US)

( * ) Notice: Subject to any disclaimer, the term of this patent is extended or adjusted under 35 U.S.C. 154(b) by 0 days.

(21) Appl. No.: 14/756,608

(22) Filed: Sep. 24, 2015

(65) Prior Publication Data

US 2016/0051659 A1  Feb. 25, 2016

Related U.S. Application Data

(63) Continuation of application No. PCT/US2013/000098, filed on Mar. 28, 2013.

(51) Int. Cl.
| | |
|---|---|
| *A61K 39/12* | (2006.01) |
| *C12N 7/00* | (2006.01) |
| *C07K 14/005* | (2006.01) |
| *A61K 9/00* | (2006.01) |
| *A61K 9/51* | (2006.01) |
| *A61K 39/00* | (2006.01) |

(52) U.S. Cl.
CPC ............ *A61K 39/12* (2013.01); *A61K 9/0019* (2013.01); *A61K 9/0021* (2013.01); *A61K 9/0073* (2013.01); *A61K 9/5115* (2013.01); *C07K 14/005* (2013.01); *C12N 7/00* (2013.01); *A61K 2039/53* (2013.01); *A61K 2039/70* (2013.01); *C12N 2760/12122* (2013.01); *C12N 2760/12134* (2013.01)

(58) Field of Classification Search
None
See application file for complete search history.

(56) References Cited

U.S. PATENT DOCUMENTS

| | | | |
|---|---|---|---|
| 5,853,980 | A | 12/1998 | Rollin et al. |
| 5,945,277 | A | 8/1999 | Nichol et al. |
| 7,217,812 | B2 | 5/2007 | Hooper |
| 2010/0323024 | A1 | 12/2010 | Hooper |

FOREIGN PATENT DOCUMENTS

| | | |
|---|---|---|
| EP | 2520582 A1 | 7/2012 |
| EP | 1529107 B1 | 10/2012 |

OTHER PUBLICATIONS

Chu, Serological relationships amound viruses n the *Hantavirus* genus, family Bunyaviridae, Virology 994; 198 (Jan. (1)): 196-204.
Fuller DH et al., Preclinical and clinical progress of particle mediated DNA vaccines . . . , Methods 2006:40 (September (a)):86-87.
Hooper et al., Hantaan/Andes virus DNA vaccine elicits a broadly cross-reactive . . . , Viroloty 2006:347 (March (1)):208-16.
Spik et al., Mixing M segment DNA vaccines to Hantaan virus . . . , Vaccine 2008; 26 (September (40)):5177-81.
Sheshberadaran, et al, Antigenic relationskp between hantaviruses analysed by immunoprecipitation, J. Gen. Virol. 1988;69 (March (Pt10);2645-51.
Arikawa, et al., Characterization of Hantaan virus envelope glycoprotein antigenic . . . , J. Gen. Virol 1989;70(March(Pt3));615-24.
Brocato, et al., 2013, Construction and nonclinical testing of a puumala virus synthetic M gene-based DNA vaccine., Clin Vaccine Immunol 20(2):218-226.
NCBI, GenBank Acession No. HI424342.1 (Nov. 9, 2010) whole document.
NCBI, GenBank accession No. DI004188.1 (Feb. 21, 2008) whole doc.
Boudreau, EF, et al., A phae 1 clinical trial Hantaan virus and Puumala virus M-segment, DNA vaccines . . . , Vaccine Mar. 2, 2012, vol. 30, No. 11, 1951-58.
Schmaljohn CS, et al.Antigenic subunits of Hanaan virus expressed by baculovirus and vaccinia virus recombinants, J. Virol 1990; 64(July(7)):3162-70.
Custer, et al., Active and passive vaccination against hantavirus pulmonary syndrome and Dndesvirus M genome . . . , J virol 2003;77(Sept(18)):9894-905.
Hooper, et al. DNA vaccination with hantavirus M segment elicits neutralizing antibodies and protects against Seoulvirus infection, Virology 1999;255(March(2)):269-78.
Schmaljohn C, Naked DNA vaccines expressing the prM and E genes of Russian spring summer encephalitis virus . . . ; J Virol 1997;71(Dec(12)):9563-9.
Roy MJ, et al., Induction of antigen specific CD8+ T cells, T helper cells . . . , Vaccine 2000;19(Nov (7-8)):764-78.
Roberts LK, et al., Clinical safety and efficacy of a powdered hepatitis B nucleic acid vaccine . . . , Vaccine 2005;23(September (40)):4867-78.
Badger CV, et al., Development and application of a flow cytometric potency assay for DNA vaccines, Vaccine 2011; (January):6728-35.
Rossi CA, et al., Enzyme-linked immunoborbent assay (ELISA). Asan Institute for Life Sciences; 1999. p. 87-98.

(Continued)

*Primary Examiner* — Benjamin P Blumel
(74) *Attorney, Agent, or Firm* — Caroline Nash; Elizabeth Arwine

(57) ABSTRACT

A synthetic, codon-optimized Hantaan virus (HTNV) full-length M gene open reading frame that consists of a unique nucleotide sequence encoding HTNV proteins. This synthetic gene was cloned into a plasmid to form the first optimized HTNV full-length M gene that elicits neutralizing antibodies in animals when delivered in combination with a similarly optimized Puumala virus (PUUV) DNA vaccine. The invention obviates the need for an extraneous gene sequence that was previously required for expression of the non-optimized HTNV gene. The synthetic gene is engineered into a molecular vaccine system to prevent hemorrhagic fever with renal syndrome (HFRS) caused by infection with HTNV, SEOV, or DOBV. Alternatively, it can be combined with the optimized PUUV DNA vaccine to protect against HFRS caused by any *hantavirus*.

18 Claims, 27 Drawing Sheets

(56) References Cited

OTHER PUBLICATIONS

Schmaljohn, et al., Antegenic and genetic properties of viruses linked to hemorrhagic fever with renal syndrome., Science 1985; 227(March (4690)):1041-4.
Chu, et al, Cross-neutralization of hantaviruses with immune sera from experimentally infected animals and from hemrrhagic . . . , J Infect Dis 1995;172(Dec(6)):1581-4.
Hooper JW, Vaccine against hantaviruses, Curr Top Microbiol Immunol 2001; 256:171-91.
Maes, P., et al., Recent approaches in hantavirus vaccine development, Expert Rev Vaccines 2009;8(January (1))):67-76.
Wang, et al. Epidemiology and surveillance programs on hemorrhagic . . . , Zhonghua Liu Xing Bing Xue Za Zhi 2010;31(June(6)):675-80.
Fang, et al. Spatiotemporaltrends and climatic factors of hemorrhagic . . . , PLoS Negl Trop dis 2010:4(8):e789.
Zhang YZ et al., Hantavirus infections in humans and animals, China Emerg Infect Dis Aug. 2010:16(August(8)):1195-203.
Heyman, Situation of hantavirus infections and haemorrhagic fever . . . , Dec. 2006, Euro Surveill 2008;13(July(28)).
Chu YK, et al., A vaccinia virus-vectored Hantaan virus vaccine protects . . . , J. Virol 1995; 69 (October (10)):6417-23.
Hooper JW, et al., DNA vaccination with the Hantaan virus M gene protects hamsters . . . , J. Virol 2001:75 (Sept (18)):8469-77.
McClain DJ, et al., Clinical evaluation of a vaccinia-vectored Hantaan virus vaccine, J. Med Virol 2000: 60(January (1)):77-85.
Schmaljohn CS, et al., Preparation of candidate vaccinia-vectored vaccines for haemorrhagic fever with renal syndrome. Vaccine 1992:10(1):10-3.

HTNV + PUUV Vaccines

FIG. 4A

HTNV + PUUV Vaccines

HTNV PRNT

Cohort 1: HTNV vaccine
7 of 11 seroconverted to HTNV

FIG. 12A

Cohort 2: PUUV vaccine
6 of 8 seroconverted to PUUV

FIG. 12B

Cohort 3: Combination HTNV/PUUV vaccines - 7 of 9 seroconverted
(3 to HTNV, 7 to PUUV, 3 to both)

FIG. 12C

Cohort 3: Combination HTNV/PUUV vaccines - 7 of 9 seroconverted
(3 to HTNV, 7 to PUUV, 3 to both)

| Group # | # of Subjects | Vaccine | Dose (mg) | Volume (ml) | Schedule (Days) |
|---|---|---|---|---|---|
| 1 | 30 | HTNV/PUUV | 2.0 | 1.0 | 0, 28, 56 (180) |
| 2 | 30 | HTNV/PUUV | 2.0 | 1.0 | 0, 56 (180) |
| 3 | 30 | HTNV/PUUV | 1.0 | 1.0 | 0, 28, 56 (180) |
| 4 | 30 | HTNV/PUUV | 1.0 | 1.0 | 0, 56 (180) |
| total | 120 | | | | |

FIG. 14

GENE OPTIMIZED HANTAAN VIRUS M SEGMENT DNA VACCINE FOR HEMORRHAGIC FEVER WITH RENAL SYNDROME

This application is a continuation of PCT/US13/00098 filed Mar. 28, 2013.

GOVERNMENT INTEREST

The invention described herein may be manufactured, used and licensed by or for the U.S. Government.

BACKGROUND OF THE INVENTION

The invention relates to a vaccine for hemorrhagic fever with renal syndrome caused by *hantavirus* infections.

The *Hantavirus* genus of the family Bunyaviridae includes a number of rodent-borne viruses that can cause hemorrhagic fever with renal syndrome (HFRS) or *hantavirus* pulmonary syndrome (HPS). At least four hantaviruses cause HFRS: Hantaan (HTNV), Seoul (SEOV), Dobrava (DOBV), and Puumala (PUUV) viruses. HFRS presents with sudden fever, chills, nausea, headache, and backache. Early symptoms of severe HFRS often also include facial flushing, conjunctivitis, and petechial rash. Death can occur due to vascular leakage leading to low blood pressure, acute shock, and renal failure. There are no FDA-licensed vaccines for HFRS, but an inactivated, rodent-brain-derived HTNV vaccine is commercially available in Korea, and several inactivated cell culture-derived HTNV and SEOV vaccines have been developed in China [1,2].

Despite the use of these vaccines for more than a decade, HFRS remains a significant public health threat in Asia with thousands of hospitalized cases reported each year in China [3-5]. Several hundred to thousands of HFRS cases due to PUUV or DOBV infections are reported each year in Europe, Scandinavia, and Russia, with the greatest incidences observed in Finland (25,000 cases from 1979 to 2006) and western Russia (~89,000 cases from 1996 [6]. Inactivated vaccines have not been developed in Europe, in part because PUUV is difficult to grow in cell culture to high enough titers for scale-up, and rodent brain-derived vaccines are not considered desirable. Moreover, because DOBV and PUUV both cause HFRS in the same geographic region, and because there is little or no cross-protective immunity between PUUV and the other HFRS-causing *hantaviruses* [7,8], a comprehensive vaccine for European HFRS will need to elicit protective immunity to both viruses.

To date, two recombinant DNA vaccines for HFRS have been tested in early clinical studies. The first tested was a vaccinia virus (VACV)-vectored vaccine, developed and evaluated in Phases 1 and 2 clinical studies by USAMRIID [9,10]. The vaccine expressed two of the three gene segments of HTNV: the M segment, which encodes the envelope glycoproteins (Gn and Gc), and the S segment, which encodes the nucleocapsid protein (N). In general, animal studies have shown that neutralizing antibodies to Gn and Gc are the best measurable correlate of protective immunity [8, 11-13]. This earlier study found that the recombinant VACV vaccine elicited neutralizing antibodies against HTNV in VACV-naïve individuals, but was poorly immunogenic in VACV-immune volunteers [9]. Consequently, the vaccine developers changed strategies to a DNA vaccine platform, which was not adversely affected by preexisting vector immunity and which offered additional flexibility for producing combination vaccines. In addition to flexibility, DNA is an attractive vaccine platform in terms of ease of engineering and manufacturing as well as safety.

USAMRIID investigators have so far conducted two Phase 1 clinical studies with DNA vaccines for HFRS using DNA derived from HTNV and from PUUV M segments. The two-part DNA vaccine strategy was used because vaccination with the HTNV M gene-based DNA vaccine protects animals from infection with HTNV, DOBV and SEOV, but not from PUUV infection. PUUV M gene-based DNA vaccine protects against infection with PUUV [7-8].

The first two clinical studies of the HTNV and PUUV DNA vaccines were performed using a PUUV M segment vaccine that was genetically optimized (US 2010/0323024A1, incorporated herein by reference in its entirety). The HTNV component, however, was not optimized, because unlike the PUUV DNA, which required optimization for gene expression, the HTNV DNA construct showed strong gene expression without optimization. It could not be anticipated, therefore, that a similar optimization was either necessary or would offer a benefit over the non-optimized DNA for immunogenicity. Further and formerly, an extraneous gene sequence was required for the expression of the non-optimized HTNV gene, U.S. Pat. No. 7,217,812, incorporated by reference, herein, in its entirety.

In the first clinical study of the DNA vaccines, HTNV and PUUV M segments were delivered by particle mediated epidermal delivery (PMED). The advantage of intraepidermal delivery of the vaccine is twofold. The DNA is easily taken up by cells at the site of delivery or by cells in the draining lymph nodes where the antigen encoded by those cells is reprocessed by specialized antigen-presenting cells to elicit an immune response, and this approach uses 1000-fold less DNA than needle administration.

The vaccines were given as separate administrations because of results from animal studies, which showed that if the HTNV vaccine is mixed with the PUUV vaccine, then only neutralizing antibodies to PUUV are elicited [25]. This finding was not expected, because it was possible to obtain strong responses to the individual vaccines or to both vaccines when they were delivered simultaneously, but as separate inoculations, to a single animal. In addition, it was not possible to overcome this interference by adjusting the ratio of HTNV: PUUV DNA even as high as 10:1 (FIG. 8B). Other attempts to produce modified constructs that were chimeras of both the HTNV and PUUV genes also failed to elicit antibody responses to both HTNV and PUUV (unpublished information). The outcome of the interference study is summarized in Example 1.

In a second Phase 1 clinical study of the same two DNA vaccines, the DNAs were given separately or as a mixture by intramuscular electroporation (IM-EP). With this delivery method, the vaccines are injected into muscles and a rapid electrical pulse is applied to facilitate uptake of the DNA into the muscle cells. Because a larger number of host cells receive the vaccines than when they are delivered by PMED, it was anticipated that there might be some response to both vaccines. As expected, however, interference was still a problem in individuals receiving the mixed vaccines, with better responses obtained to the PUUV vaccine than to the HTNV vaccine as shown in Example 2.

Delivery of the vaccine can also be by nanoparticle encapsulation of the vaccine via various methods, including aerosol delivery of the nanoparticles.

The present invention provides a combination vaccine to protect against HFRS. The invention consists of an optimized HTNV M segment vaccine, which solves the problem of interference in the bivalent vaccine. Unlike the non-optimized HTNV vaccine used in previous studies, the vaccine of the invention can be mixed with a similarly optimized PUUV-based vaccine to elicit neutralizing antibodies against both viruses. The invention provides a safe, economical, flexible and effective vaccine for the protection of humans from HFRS caused by infection with HTNV, SEOV, PUUV and/or DOBV.

SUMMARY OF THE INVENTION

The invention is a synthetic, optimized HTNV M segment DNA vaccine that is superior to the earlier non-optimized HTNV DNA vaccine and can be used by itself to prevent HFRS caused by three hantaviruses: (HTNV, SEOV or DOBV) or in combination with the optimized PUUV DNA vaccine to protect from all four HFRS causing hantaviruses. The synthetic optimized HTNV DNA does not require extraneous, superfluous nucleotides for expression and immunogenicity and can be delivered as a mixture with other *hantavirus* vaccines without reduced immunogenicity or protective efficacy in animal models. To improve the vaccine component, the HTNV DNA vaccine was optimized to maximize mammalian codon availability and to remove viral elements shown to compromise expression.

BRIEF DESCRIPTION OF THE FIGURES

Figures 4A, 4B:
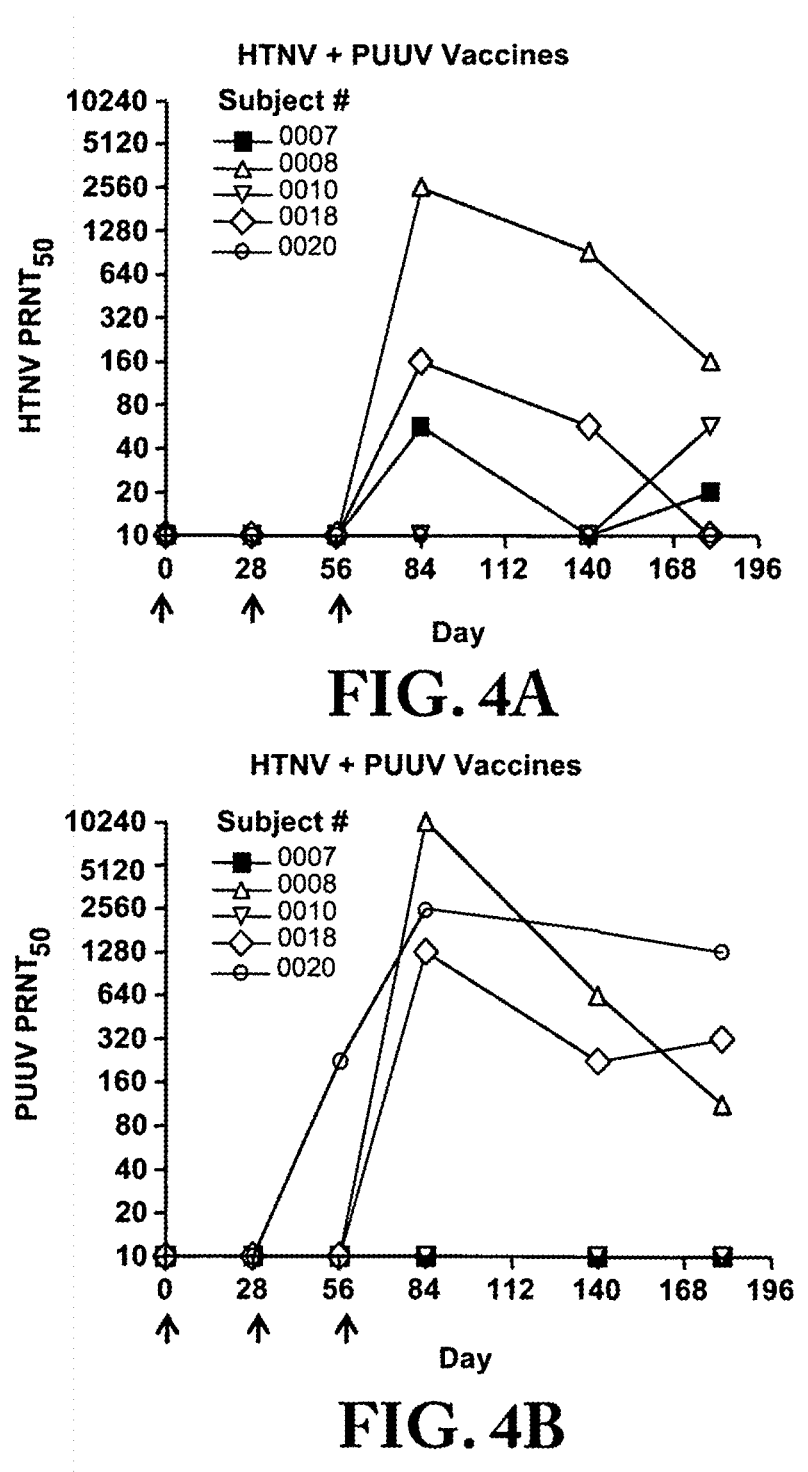

FIG. 4A is a graph showing neutralizing antibody responses to HTNV of subjects receiving separate administrations of the non-optimized HTNV DNA vaccine and the optimized PUUV vaccine with each symbol representing the neutralizing antibody (PRNT$_{50}$) titer for subjects listed in the legend and arrows indicating vaccination days, showing that separate administrations of both the HTNV and PUUV DNA vaccines to a single individual can induce antibody responses to HTNV;

FIG. 4B is a graph showing neutralizing antibody responses to PUUV of subjects receiving separate administrations of the non-optimized HTNV DNA vaccine and the optimized PUUV vaccine with each symbol representing the PRNT$_{50}$ titer for subjects listed in the legend and arrows indicating vaccination days, showing that separate administrations of both the HTNV and PUUV DNA vaccines to a single individual can induce antibody responses to PUUV;

FIG. 7A is a digital photograph showing HTNV protein (green color) produced by the optimized HTNV M segment vaccine (HTNV M) and detected by immunofluorescent antibody staining with a monoclonal antibody to HTNV;

FIG. 7B is a digital photograph showing HTNV protein (green color) produced by the non-optimized HTNV M segment vaccine (HTNV M (x)) and detected by immunofluorescent antibody staining with a monoclonal antibody to HTNV;

FIG. 7C is a graph from a flow cytometry assay showing expression of the optimized HTNV M segment DNA synthesized to also contain the extraneous nucleotides found in the non-optimized HTNV M vaccine as compared to the same DNA synthesized without the extraneous sequences;

FIG. 8B is a graph showing neutralizing antibodies to HTNV of hamsters vaccinated with the non-optimized HTNV DNA vaccine alone, the optimized PUUV DNA vaccine alone or 1:1, 2:1 or 10:1 mixtures of the non-optimized HTNV DNA and the optimized PUUV DNA vaccines using two types of intramuscular IM-EP devices or one type of ID-EP device, showing that PUUV DNA does interfere with HTNV DNA immunogenicity;

FIG. 9 is a graph showing immunogenicity (specific neutralizing antibodies) in hamsters of optimized HTNV DNA vaccine of the invention compared to the non-optimized HTNV DNA, the optimized PUUV DNA vaccine or a 1:1 mixture of both optimized DNA vaccines delivered to hamsters by ID-EP, showing that the optimized HTNV DNA has overcome interference problems associated with the non-optimized HTNV DNA;

FIG. 11A is a graph showing neutralizing antibodies to PUUV of individual rabbits vaccinated by intramuscular electroporation with non-optimized HTNV DNA vaccine (pWRG/HTN-M(x) as compared to the PUUV DNA vaccine (pWRG/PUU-M(s2) or a mixture of the two vaccines (Combination) showing equivalent neutralizing antibody titers to PUUV;

FIG. 11B is a graph showing neutralizing antibodies to HTNV of individual rabbits vaccinated by IM-EP with non-optimized HTNV DNA vaccine (pWRG/HTN-M(x) as compared to the PUUV DNA vaccine (pWRG/PUU-M(s2) or a mixture of the two vaccines (Combination) showing evidence of interference;

FIG. 12A is a graph showing neutralizing antibody responses to HTNV of humans vaccinated with the non-optimized HTNV DNA vaccine by IM-EP;

FIG. 12B is a graph showing neutralizing antibody responses to PUUV of humans vaccinated with the optimized PUUV DNA vaccine by IM-EP;

FIG. 12C is a graph showing neutralizing antibody responses to HTNV of humans vaccinated with a 1:1 mixture of non-optimized HTNV and optimized PUUV DNA vaccines by intramuscular electroporationIM-EP; indicating reduced number of responses to HTNV and evidence of interference with HTNV immunogenicity.

FIG. 12 D is a graph showing neutralizing antibody responses to PUUV of humans vaccinated with a 1:1 mixture of non-optimized HTNV and optimized PUUV DNA vaccines by intramuscular electroporationIM-EP; indicating no interference with PUUV immunogenicity.

FIG. 13 is a graph showing a hamster study showing the results of geometric mean titers of neutralizing antibodies to each of four hantaviruses known to cause hemorrhagic fever with renal syndrome in hamsters vaccinated with the optimized HTNV DNA vaccine alone, the optimized PUUV DNA vaccine alone or a mixture of the optimized HTNV and PUUV DNA vaccines indicating that the optimized HTNV vaccine induces antibodies to HTNV, SEOV, and DOBV, but not to PUUV); the optimized PUUV vaccine elicits antibodies only to PUUV, but that the mixture of the optimized HTNV and PUUV vaccines induces neutralizing antibodies to all four of the hantaviruses;

FIG. 14 is a table showing a study design for an ongoing clinical study in 120 subjects vaccinated with two doses and at two schedules by IM-EP with the mixed optimized HTNV and PUUV DNA vaccines;

DETAILED DESCRIPTION

A recombinant DNA-based vaccine for HTNV and PUUV M segments constructs circumvents key issues associated with both production and formulation of combination vaccines for HFRS. The invention provides a bivalent vaccine for all HFRS-causing viruses, which includes both HTNV and PUUV M segment constructs.

The invention is a new synthetic, codon-optimized HTNV full-length M gene open reading frame (ORF) that encodes amino acids forming viral proteins. The optimization of the gene has solved a long felt need in this type of vaccine, namely major gene related interference with former vaccines, which prevented development of a comprehensive vaccine for HFRS. Determining how to optimize and produce a synthetic gene for the HTNV M segment required extensive testing.

This synthetic gene was cloned into a plasmid to form the first HTNV full-length M gene that elicits neutralizing antibodies in animals when delivered in combination with a similarly optimized PUUV DNA vaccine (U.S. patent publication US2010/0323024A1, incorporated herein by reference). In addition, the invention obviates the need for an extraneous gene sequence that was previously found to be required for expression of the non-optimized HTNV gene. The synthetic gene is engineered into a molecular vaccine system to prevent HFRS caused by infection with HTNV, SEOV or DOBV. Alternatively, it can be combined with the optimized PUUV DNA vaccine to protect against HFRS caused by any *hantavirus*.

Specifically, the invention consists of a genetically modified DNA vaccine representing the open reading frame of the M genome segment of the HTNV that has been optimized to include several features known to increase mammalian expression. See SEQ ID NO. 1

Figure 6:
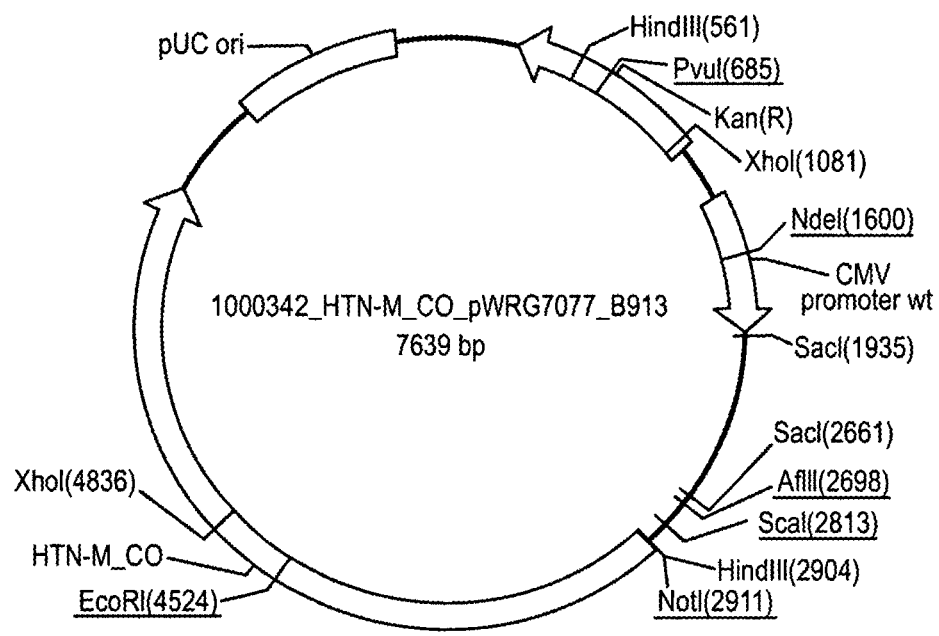
FIG. 6 is a plasmid map of the synthetic gene HTN-M_CO, consisting of 3415 base pairs assembled from synthetic oligonucleotides and/or PCR products into a pWRG7077 plasmid.

The HTNV DNA vaccine expresses the envelope protein genes of HTNV that were adapted to the codon bias of *Homo sapiens* genes. The codon adaption index, which describes how well the codons match the codon usage preference of *homo sapiens*, where 1.0 is perfect, was increased for the HTNV gene from 0.67 to 0.97. In addition, regions of the very high (>80%) or very low (<30%) guanine-cytosine (GC) content were avoided in the genes where possible as either extreme results in poor expression. For the HTNV gene, the average GC content was increased from 40% to 60%, to prolong mRNA half-life. Also, negative cis-acting motifs, such as splice sites, poly(A) signals, TATA-boxes, etc. which may negatively influence expression were eliminated where possible. The optimized HTNV gene open reading frame was then synthesized by Geneart, Inc. (Regensburg, Germany) and inserted between the NotI and BglII restriction sites of plasmid backbone pWRG7077 [30] (to create the DNA vaccine construct that comprise the invention (See FIG. 6). The pWRG7077 plasmid backbone (pWRG7077 (4326 bp) (PowderJect Vaccines, Inc., Madison, Wis.) contains the human cytomegalovirus immediate early (CMV IE) promoter with its associated Intron A, a bovine growth hormone transcription terminator and polyadenylation signal (BGH pA), a pUC19 origin of replication (ori), and a kanamycin resistance marker (KanR) shown in FIG. 6. The complete nucleotide sequence of the final HTNV DNA vaccine construct has been confirmed as shown in SEQ ID No. 1.

Figures 7A, 7B:
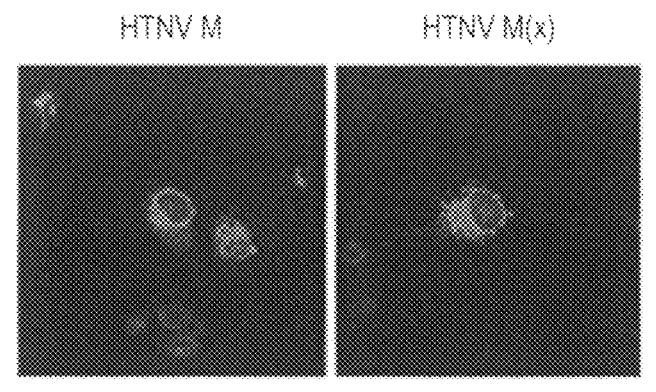
Figure 7C:
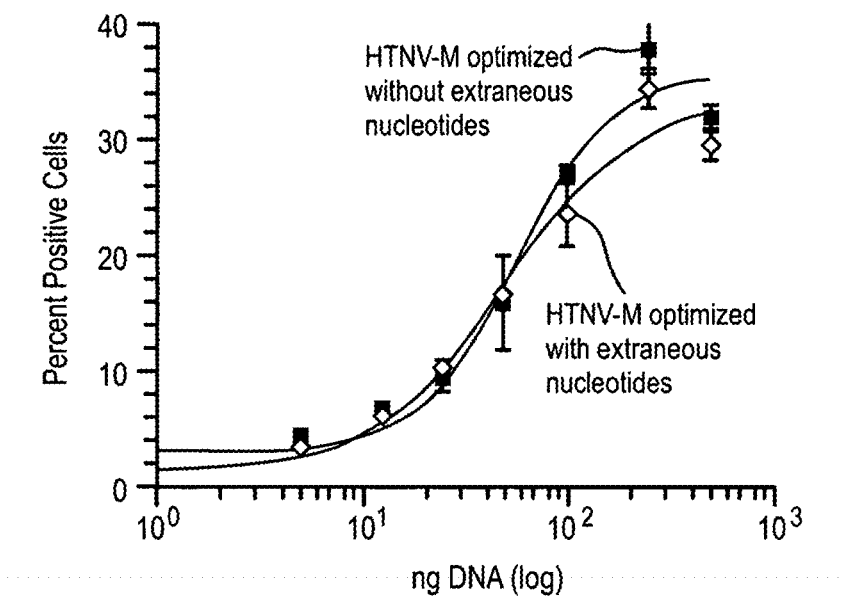

The optimized HTNV DNA vaccine produces HTNV protein that can be recognized in immunofluorescent antibody assays and by flow cytometry when reacted with a monoclonal antibody to a HTNV envelope glycoprotein (FIG. 7A). In addition, the HTNV gene that comprises the invention shows comparable expression in cell cultures to the previously developed, non-optimized HTNV M DNA vaccine, which has non-coding extraneous nucleotides that are required for expression (FIG. 7B). The optimized gene in this invention does not require the extraneous nucleotides for expression, and addition of these nucleotides to the construct does not improve expression. As shown in FIG. 7C, a flow cytometry comparison of the optimized HTNV M that were synthesized with or without the extraneous nucleotides had the same expression profiles. Therefore, the invention is an improvement over the earlier DNA vaccine construct in that it does not require the presence of noncoding nucleotides to produce HTNV proteins.

Figure 7D:
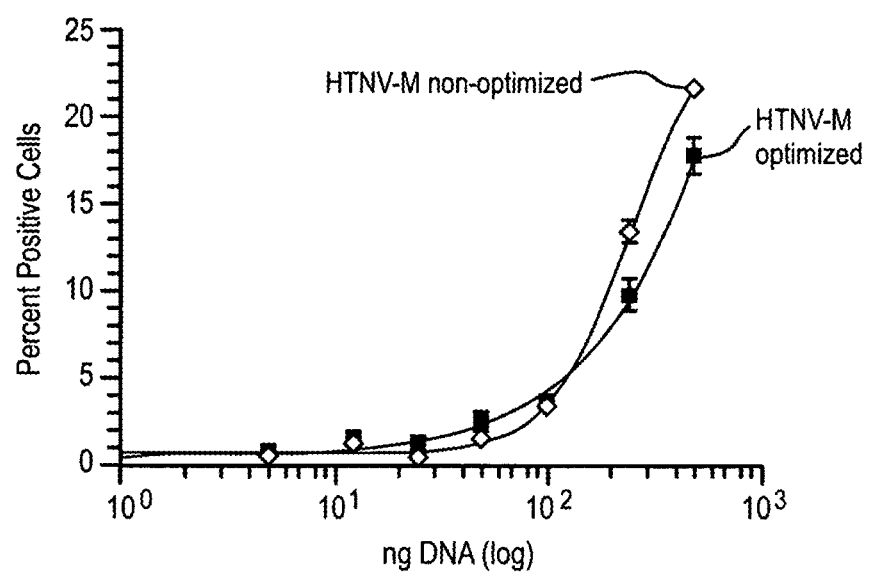
FIG. 7D is a graph from a flow cytometry assay showing expression of the synthetic optimized HTNV M segment DNA compared to the non-optimized DNA.

In FIG. 7D, flow cytometry was performed in order to compare expression of the non-optimized (original) HTNV M DNA to the optimized (HTNV_M_CO) DNA. Two curves are shown, which represent independent analysis. The synthetic gene has a similar expression profile as that of the original gene. Conclusions were that the synthetic gene produces HTNV proteins that are recognized by antibodies to authentic HTNV and expression does not require the presence of the extraneous nucleotides that must be present for expression of the original gene.

Of primary importance for this invention, the new synthetic DNA vaccine construct solves a major gene-related interference problem, which prevented development of a comprehensive vaccine for HFRS. That is, in order to elicit protective immunity against all four hantaviruses that are able to cause HFRS, it is necessary to vaccinate with both the HTNV DNA vaccine and also with the PUUV DNA vaccine[28, 29]. However, when the native M segment HTNV DNA vaccine was delivered to test animals in combination with the PUUV M segment DNA vaccine, the animals developed antibody responses only to the PUUV component (FIG. 8, and [31]). It was not possible to overcome this interference by increasing the ratio of HTNV to PUUV DNA in the mixture (FIG. 8B).

Figure 8A:
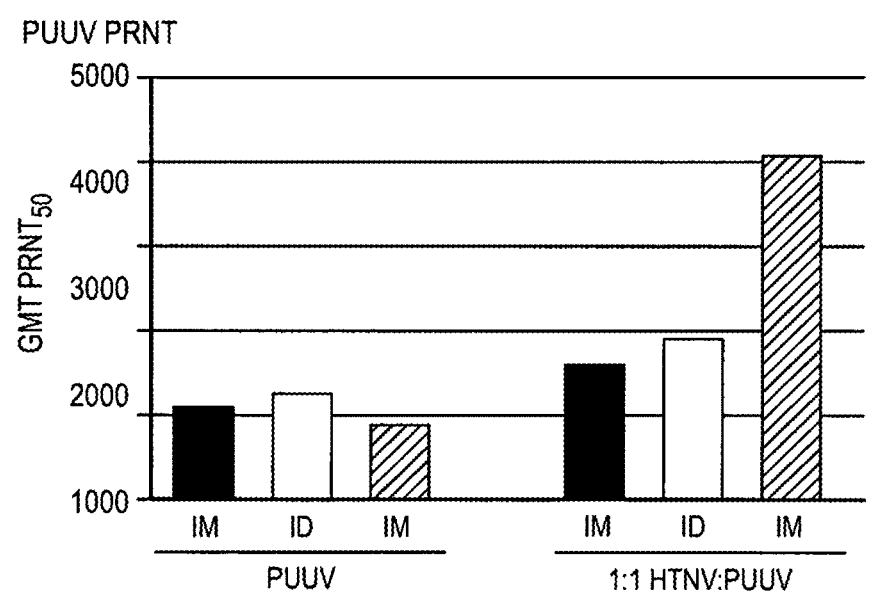
FIG. 8A is a graph showing neutralizing antibodies to PUUV of hamsters vaccinated with the optimized PUUV DNA vaccine or a 1:1 mixture of the optimized PUUV vaccine and the non-optimized HTNV using two types of IM-EP devices or one type of intradermal (ID) EP device, showing that HTNV DNA does not interfere with PUUV DNA immunogenicity.
Figure 8B:
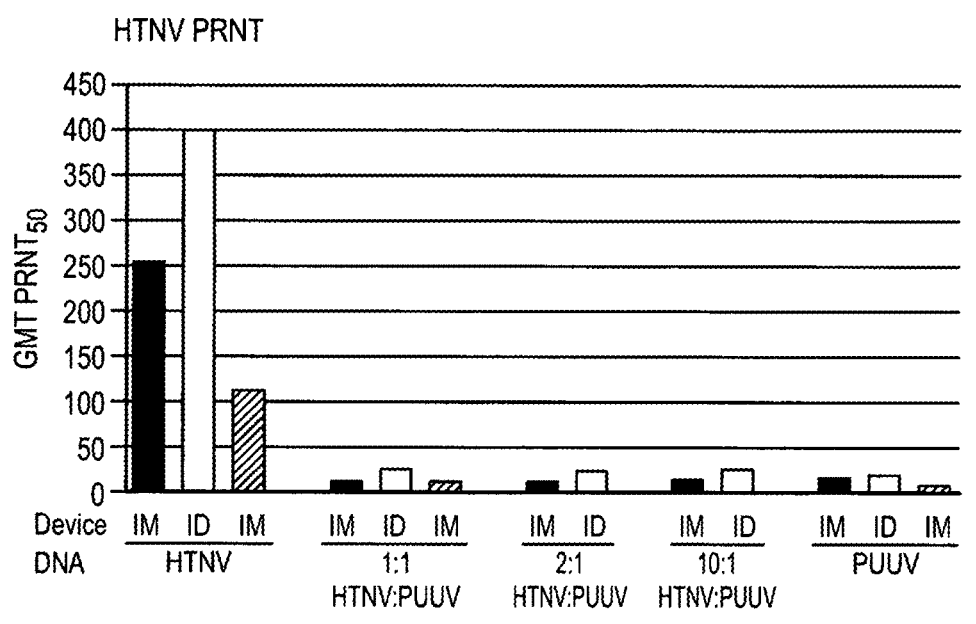

In FIGS. 8A and 8B, there is shown immunogenicity of HTNV DNA vaccines delivered to hamsters using two types of IM-EP devices or one type of ID-EP device. In FIG. 8A, shown are geometric mean titers (GMT) of neutralizing antibodies to PUUV measured by plaque reduction neutralization test (PRNT) of serum from hamsters vaccinated with optimized PUUV DNA or with a 1:1 mixture of non-optimized HTNV and optimized PUUV DNA. The hamsters develop neutralizing antibodies to PUUV in all groups, indicating that non-optimized HTNV DNA does not interfere with optimized PUUV DNA immunogenicity. In FIG. 8B, there is shown GMT of neutralizing antibodies to HTNV measured by PRNT of serum from hamsters vaccinated with non-optimized HTNV DNA or with 1:1, 2:1 or 10:1 mixtures of non-optimized HTNV and optimized PUUV DNA or with optimized PUUV DNA. Results show that the non-optimized HTNV vaccine elicits neutralizing antibodies to HTNV in hamsters, but that the optimized PUUV vaccine and the mixed vaccines do not, indicate in the PUUV vaccine alone cannot elicit antibody responses to HTNV in hamsters and that mixing the PUUV vaccine with the non-optimized HTNV vaccine results in interference with the immunogenicity of the non-optimized HTNV vaccine. Titers shown are the reciprocal of the dilution of sera required to reduce plaque counts of controls by 50%.

In contrast, using this invention, it is possible to obtain neutralizing antibodies against both HTNV and PUUV in animals that receive the mixed vaccine. In addition, this new optimized HTNV DNA vaccine is at least as effective or more effective than the non-optimized HTNV DNA vaccine at eliciting antibody responses against HTNV when given alone. See FIG. 9. More specifically, in FIG. 9, there is shown the immunogenicity of optimized HTNV of the invention and PUUV DNA vaccines (US 2010/0323024 A1), incorporated herein in its entirety by reference, delivered to hamsters by ID-EP. Geometric mean titers (GMT) of neutralizing antibodies to homologous viruses (first three bars) were measured using sera from hamsters vaccinated with the codon-optimized HTNV DNA vaccine, the non-optimized HTNV DNA vaccine, or the codon-optimized PUUV DNA vaccine. GMT titers to HTNV (fourth bar) or to PUUV (last bar) were measured in sera from hamsters vaccinated with a 1:1 mixture of the optimized HTNV and PUUV M segment optimized DNA vaccines. Titers shown are the reciprocal of the dilution of sera required to reduce plaque counts of controls by 50%.

Delivery:

To accelerate the immune response to the vaccines, the vaccine is delivered using a state-of-the art technology component, electroporation (EP). The DNA is formulated in an excipient approved for human delivery, such as sterile normal saline or other inert substance as a carrier. Both intramuscular (IM) and intradermal (ID) EP devices are available and both have been found to notably enhance the immunogenicity of the HFRS vaccines in animals. ID-EP delivery may be used, which not only capitalizes on the efficient delivery of EP, but also offers the advantages of reduced cost and logistics for mass vaccinations. This bivalent vaccine, in combination with EP delivery accelerates the immune response to the hantaviruses and reduce the number of dosings needed to achieve protective immunity as compared to delivery without EP.

Other delivery methods include jet injection and nanoparticle encapsulation.

To measure the safety of the vaccine in controlled studies under Good Laboratory Practice (GLP) conditions, rabbits are vaccinated with either IM-EP or ID-EP of the optimized vaccine given alone or in combination with the PUUV DNA vaccine. Two manufacturers' EP devices have been tested with the *hantavirus* DNA vaccines (Ichor and Inovio) in hamsters and both have produced excellent results. IM-EP has been tested more extensively in humans than ID-EP, and is currently the gold standard delivery method for DNA vaccines; however, ID-EP has been found to elicit stronger immune responses than IM-EP for some pathogens because skin is a highly immunologically active organ with numerous circulating antigen presenting cells. In addition to possibly improving immunogenicity with ID-EP, skin vaccination is a desired delivery platform for mass vaccination with biodefense vaccines. Current clinical IM-EP delivery requires loading of DNA vaccine into the delivery device at the time of delivery, whereas the ID-EP platform consists of preloaded disposable cartridges containing the DNA vaccines, which can be administered using a re-useable EP device. The prototype ID-EP device has already been tested in a successfully completed GLP non-clinical safety study in rabbits and humans with another biodefense-related DNA vaccine for Venezuelan equine encephalitis virus.

Together the vaccine and EP delivery platform proposed offers expedient scale-up, long term stability, reduced cold-chain requirements, and mass vaccination applicability.

Safety Study:

A safety study in rabbits was used to obtain approval for testing of the combined non-optimized HTNV and optimized PUUV DNA vaccines in humans. A human study was also recently completed with no serious adverse events related to the vaccines reported. Similarly, a second safety study, also to be performed in rabbits, will be used in support of a pending IM-EP vs ID-EP Phase 1 clinical study with the optimized HTNV DNA vaccine alone and in combination with the optimized PUUV vaccine. The rabbit study characterizes local and/or systemic adverse responses associated with optimized HTNV and/or PUUV vaccine candidates administered using the IM-EP and ID-EP devices. A summary of the repeat dose safety and toxicity study design is shown in Table 1.

TABLE 1

Summary of Repeat Dose Safety/Toxicity Study Design

| Group | Vaccine | Delivery | Dose | Injection # & Volume | Admin. Schedule | N (M/F) | Endpoint |
|---|---|---|---|---|---|---|---|
| 1 | HTNV | IM-EP | 3.0 mg | 1 × 1000 µl | 0, 14, 28, 56 | 20 (10/10) | 5M/5F: Day 58<br>5M/5F: Day 70 |
| 2 | HTNV | ID-EP | 1.2 mg | 2 × 200 µl | 0, 14, 28, 56 | 20 (10/10) | 5M/5F: Day 58<br>5M/5F: Day 70 |
| 3 | HTNV + PUUV | IM-EP | 6.0 mg | 1 × 1000 µl | 0, 14, 28, 56 | 20 (10/10) | 5M/5F: Day 58<br>5M/5F: Day 70 |
| 4 | HTNV + PUUV | ID-EP | 2.4 mg | 2 × 200 µl | 0, 14, 28, 56 | 20 (10/10) | 5M/5F: Day 58<br>5M/5F: Day 70 |
| 5 | PUUV | ID-EP | 1.2 mg | 2 × 200 µl | 0, 14, 28, 56 | 20 (10/10) | 5M/5F: Day 58<br>5M/5F: Day 70 |
| 6 | Vehicle (carrier) | IM-EP & ID-EP (no EP) | Saline | 1 × 1000 µl (IM)<br>2 × 200 µl (ID) | 0, 14, 28, 56 | 20 (10/10) | 5M/5F: Day 58<br>5M/5F: Day 70 |

The invention uses cGMP manufacturing for both the safety study in rabbits and the pending clinical study. The cGMP manufacturing is conducted at a contract research organization and includes extensive release testing for potency, purity and stability, prior to use in the Phase 1 clinical trial.

Clinical Trial

To assess the safety of the optimized HTNV and PUUV DNA vaccines, 6 groups of 10 subjects each for a total of 60 subjects and 12 alternate subjects are vaccinated with the optimized HTNV vaccine, the optimized PUUV vaccine or a mixture of both vaccines. Subjects in one group receive the HTNV DNA vaccine candidate administered using the TDS-IM-EP delivery device (3.0 mg dose). Two other groups receive either the HTNV or PUUV DNA vaccines delivered by the ID-EP device (0.6 mg dose), and two groups receive the HTNV-PUUV mixed vaccine candidate administered using the IM-EP (6.0 mg total dose) or ID-EP device (1.2 mg total dose). Ten subjects receive a placebo control (5 by ID-EP, 5 by IM-EP). Note that differences in dose levels for the two routes of administration are due to the difference in volume of injection that will be administered by the respective routes (0.2 ml ID versus 1.0 ml IM).

Example 1

Non-Optimized HTNV Study, in which HTNV and PUUV Vaccines are Delivered as Separate Administrations Candidate DNA vaccines for hemorrhagic fever with renal syndrome expressing the envelope glycoprotein genes of Hantaan (HTNV) or Puumala (PUUV) viruses were evaluated in an open-label, single-center Phase 1 study consisting of three vaccination groups of nine volunteers. The volunteers were vaccinated by particle-mediated epidermal delivery (PMED) three times at four-week intervals with the HTNV DNA vaccine, the PUUV DNA vaccine or both vaccines. At each dosing, the volunteers received 8 µg DNA/4 mg gold. There were no study-related serious adverse events, and all injection site pain was graded as mild. The most commonly reported systemic adverse events were fatigue, headache, malaise, myalgia, and lymphadenopathy. Blood samples were collected on days 0, 28, 56, 84, 140, and 180, and assayed for the presence of neutralizing antibodies. In the single vaccine groups, neutralizing antibodies to HTNV or PUUV were detected in 30% or 44% of individuals, respectively. In the combined vaccine group, 56% of the volunteers developed neutralizing antibodies to one or both viruses. These results demonstrate that the HTNV and PUUV DNA vaccines are safe and can be immunogenic in humans when delivered as separate administrations by PMED (FIGS. 1, 2A, 2B, 3, 4A, 4B, 5).

Figure 1:
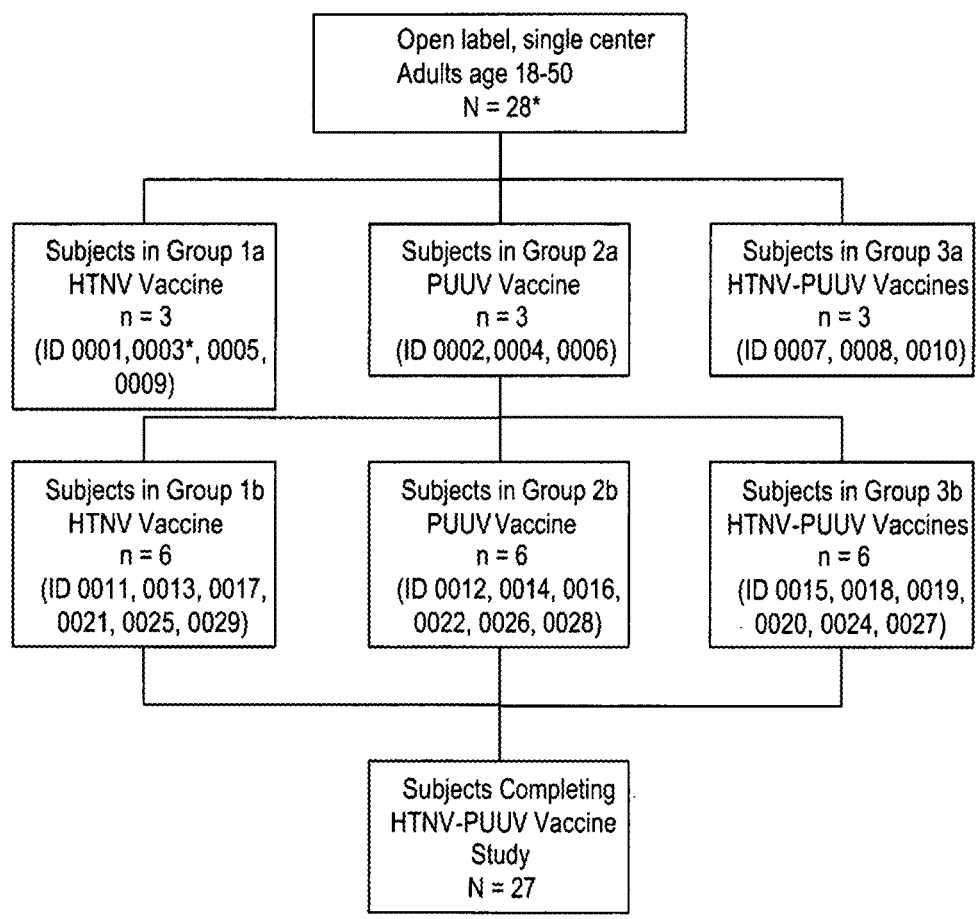
FIG. 1 is a flowchart showing a Phase 1 clinical study design wherein all vaccinations with the non-optimized HTNV DNA vaccine and the optimized PUUV DNA vaccine were administered intradermally using the ND 10 PMED device.
Figure 2A:
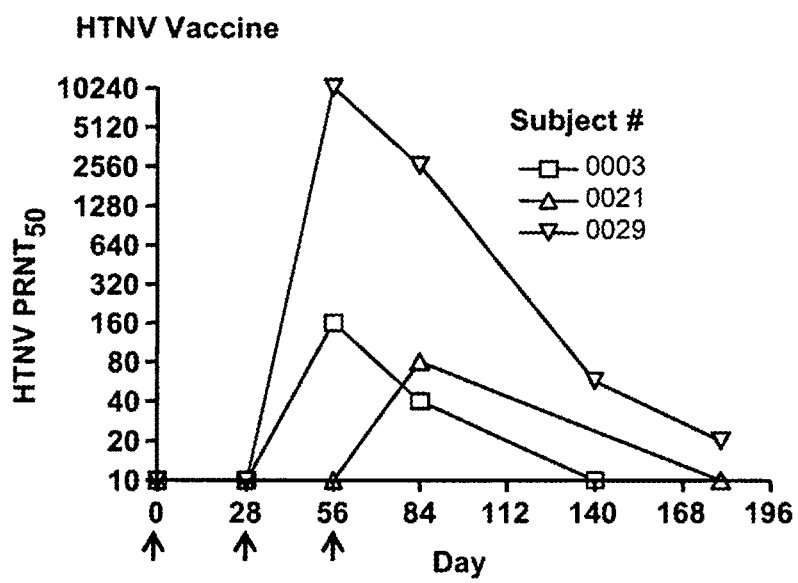
FIG. 2A is a graph of neutralizing antibody titers measured in serum samples collected from subjects vaccinated with the non-optimized HTNV vaccine.
Figure 2B:
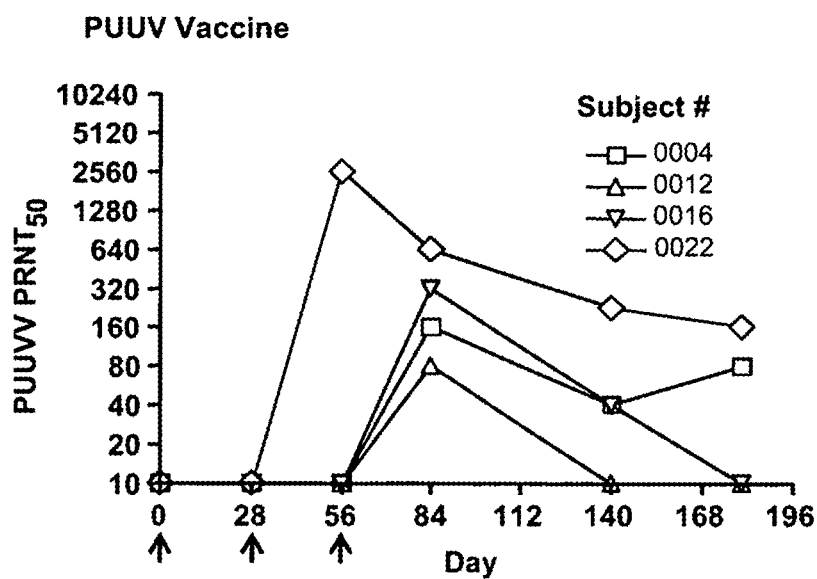
FIG. 2B is a graph of neutralizing antibody titers measured in serum samples collected from subjects vaccinated with the optimized PUUV vaccine.
Figure 3:
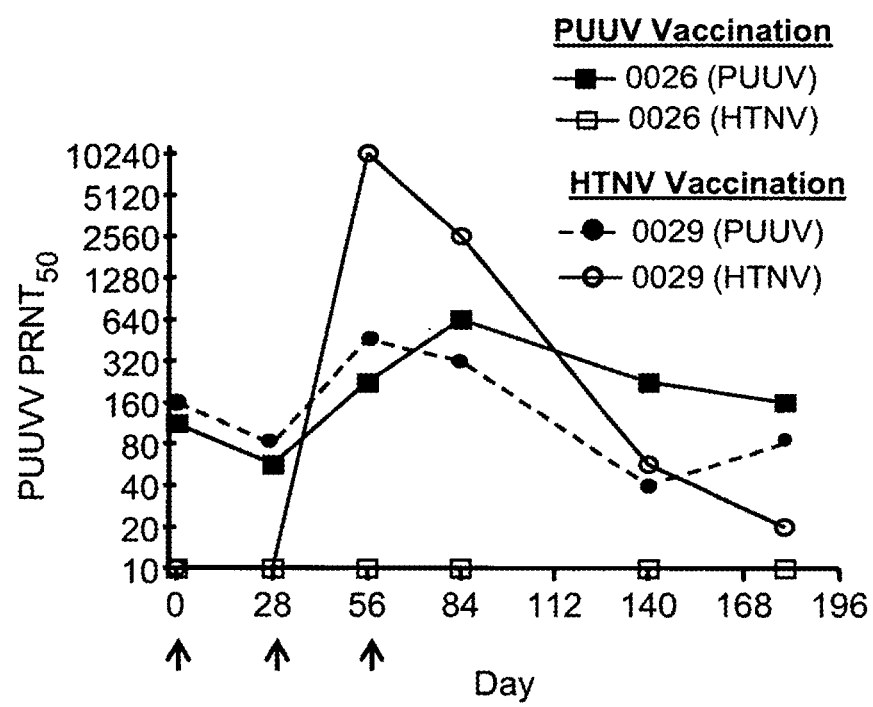
FIG. 3 is a graph showing neutralizing antibodies in blood samples collected on multiple days from two subjects vaccinated with either the optimized PUUV vaccine (subject 0026) or the non-optimized HTNV vaccine (subject 0029) with each symbol representing the neutralizing antibody (PRNT$_{50}$) titer for subjects listed in the legend and arrows indicating vaccination days, The graph shows that the optimized PUUV vaccine induced neutralizing antibodies to PUUV (closed squares) but not to HTNV (open squares). Likewise, the non-optimized HTNV vaccine induced antibodies to HTNV (open circles), but did not cause a rise in antibodies to PUUV (closed circles) even though the subject had low pre-existing antibodies to PUUV (dashed line).
Figure 5:
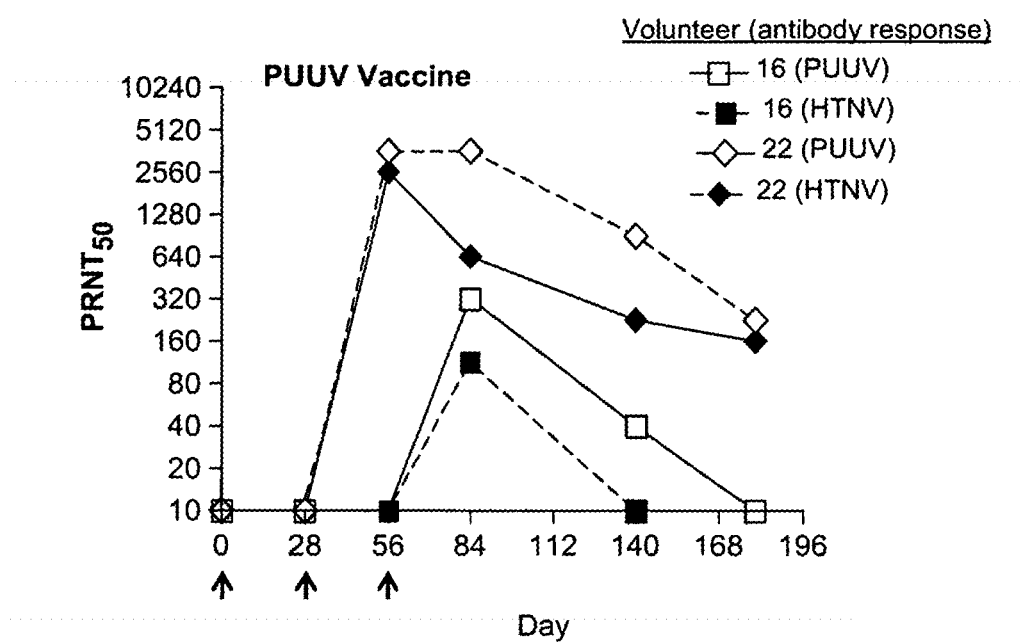
FIG. 5 is a graph showing two individuals vaccinated with the optimized PUUV DNA that developed antibodies to both HTNV and PUUV.

As shown in FIG. 3, neutralizing antibodies to PUUV detected in all samples of two subjects, indicating that there was a pre-existing exposure to a *hantavirus* prior to the start of this study; But when the person with the pre-existing antibodies to PUUV was vaccinated with the non-optimized HTNV vaccine, they had minimal response to the non-optimized HTNV vaccine, providing evidence that there is no boost in antibody response (i.e. interference in developing HTNV antibodies) even in individuals that have pre-existing antibodies to PUUV;

Example 2

Non-Optimized HTNV Study, in which the HTNV and PUUV DNA Vaccines are Given as a Mixture, Resulting in Interference In this study, vaccines were delivered using Ichor medical System's IM-EP device. The study included 3 randomized groups of 9 subjects, each of whom received three vaccinations at days 0, 28, and 56 with 2 mg of DNA/1 mL of the non-optimized HTNV vaccine, the optimized PUUV vaccine, or a mixture of both vaccines. Three vaccinations were given four weeks apart. No serious adverse events related to the vaccine were observed. Analysis of blinded serum samples indicated that neutralizing antibodies were elicited against both HTNV and PUUV, but that in volunteers receiving both vaccines, interference was observed, with only three subjects developing neutralizing antibodies to HTNV (FIG. 12C) as compared to seven developing neutralizing antibodies to PUUV (FIG. 12D).

Example 3

Figure 11A:
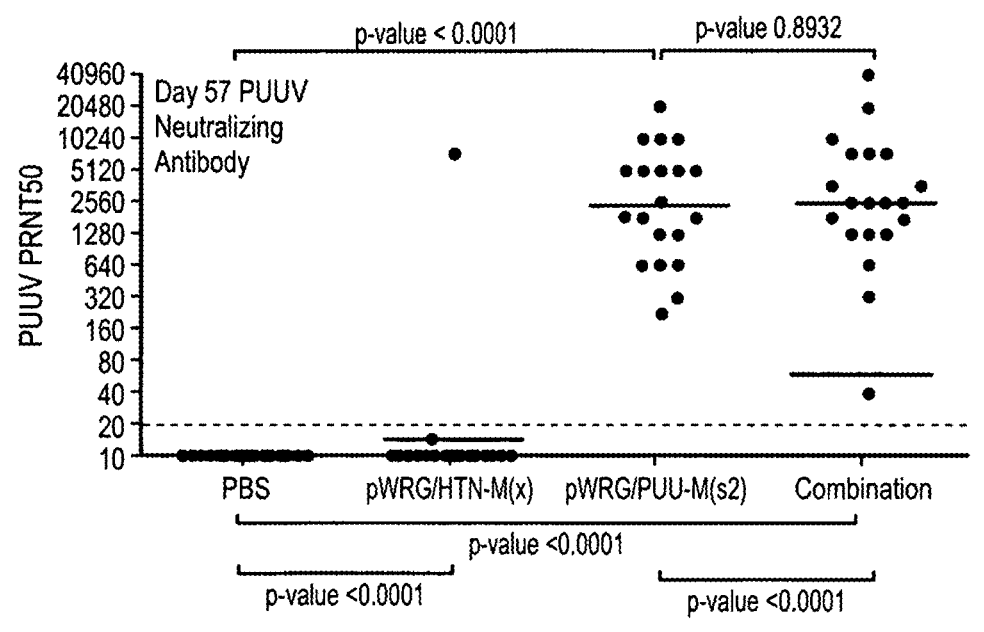
Figure 11B:
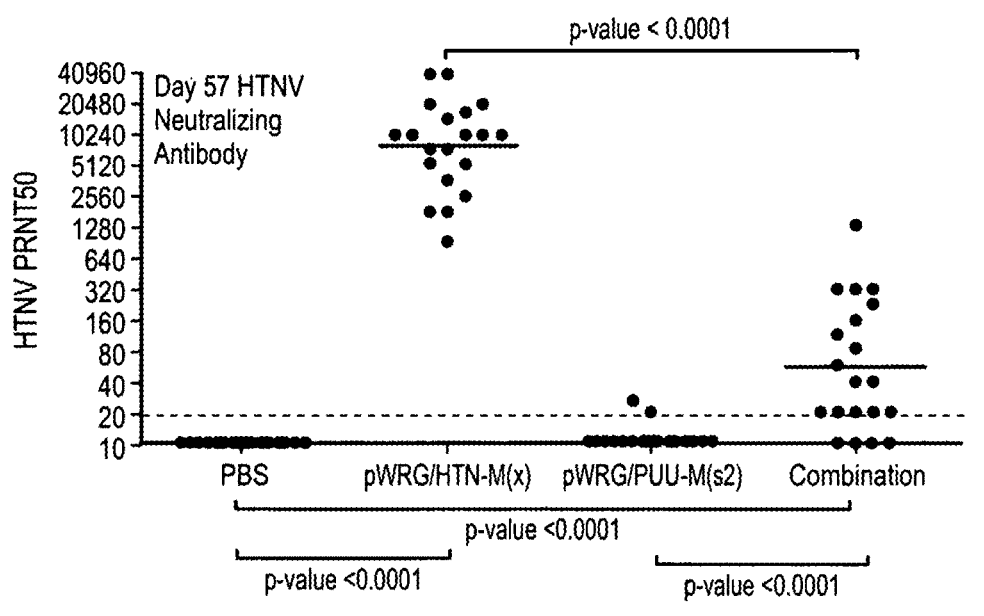

Non-Optimized HTNV DNA Preclinical Safety Study in Rabbits Showing that Mixed HTNV and PUUV DNA Vaccines Result in Reduced Response to HTNV in Rabbits, i.e., Interference In FIGS. 11A and 11B, results from a GLP safety study of non-optimized HTNV DNA vaccine and optimized PUUV DNA are shown. The vaccine delivered to rabbits by electroporation was performed. Rabbits were vaccinated three times by IM-EP with individual or mixed vaccines (1 mg each) and neutralizing antibodies were measured. Control rabbits were vaccinated with phosphate buffered saline (PBS) using IM-EP for delivery. The data show that equivalent neutralizing antibody titers to PUUV were elicited when the PUUV vaccine, pWRG/PUUM(s2), is given alone or mixed with the non-optimized HTNV DNA vaccine, pWRG/HTNM(x) (FIG. 11A); however, greatly reduced titers to HTNV were observed with the mixed vaccines as compared to those obtained with the HTNV DNA vaccine alone (FIG. 1B).

Example 4

Figure 9:
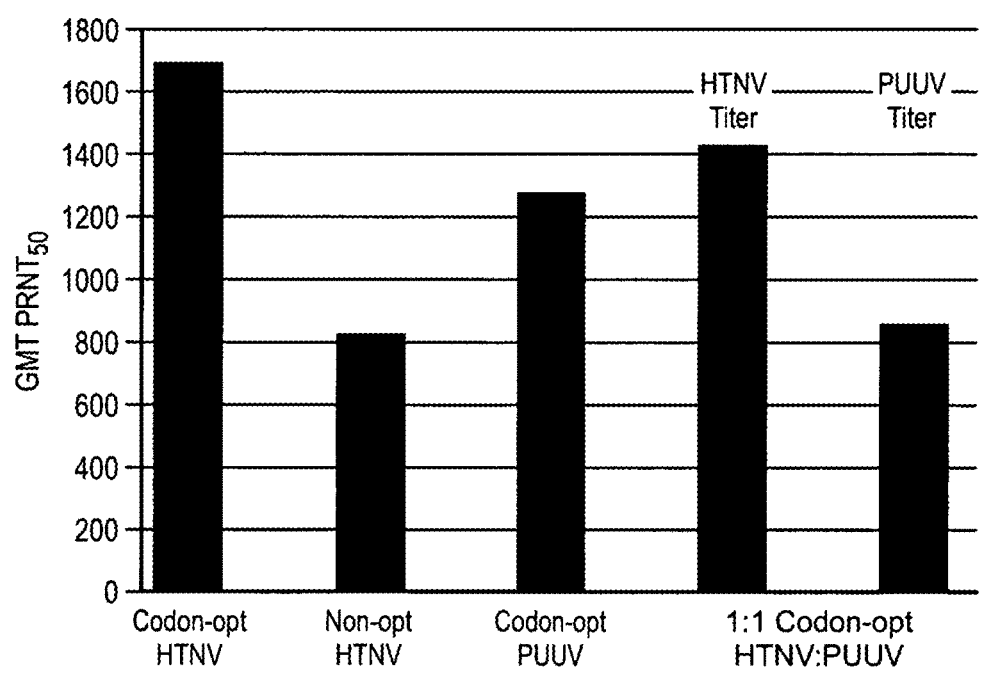
Figure 10:
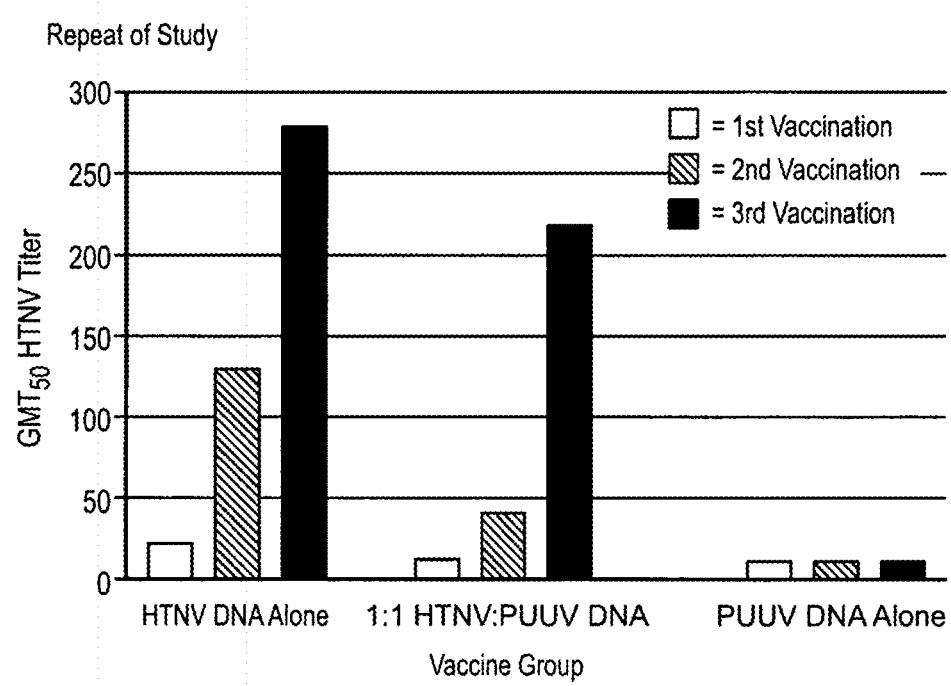
FIG. 10 is a graph showing the immunogenicity (neutralizing antibodies to HTNV) in hamsters vaccinated by electroporation with the optimized HTNV DNA vaccine alone, a 1:1 mixture of the optimized HTNV and PUUV DNA vaccines, or the optimized PUUV DNA vaccine alone after each of three sequential vaccinations, indicating that the optimized HTNV vaccine and the mixture of the optimized HTNV and PUUV DNA vaccines induce neutralizing antibodies to HTNV, but that the optimized PUUV DNA vaccine alone does not elicit neutralizing antibodies to HTNV.
Figure 15A:
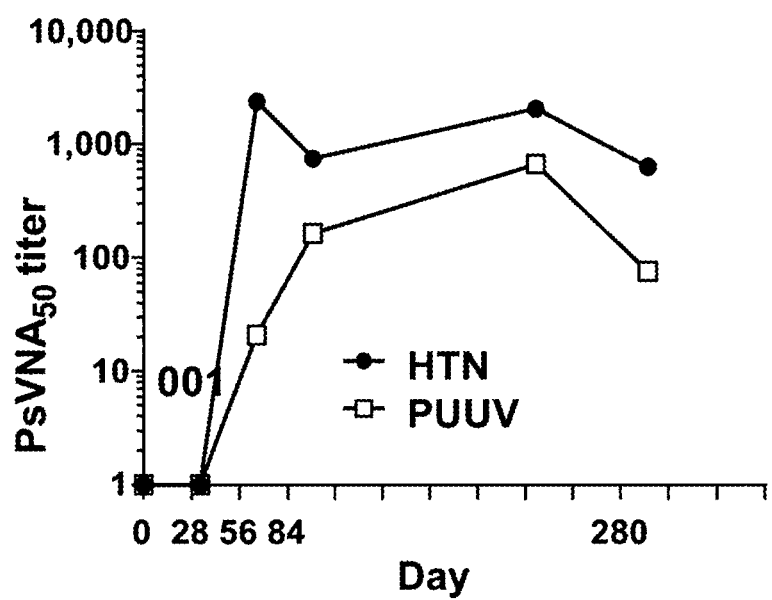
FIG. 15A is a graph showing showing pseudovirion neutralization titers from the clinical study in individual 001 responding to both of the optimized vaccines delivered as a mixture by IM-EPe.
Figure 15B:
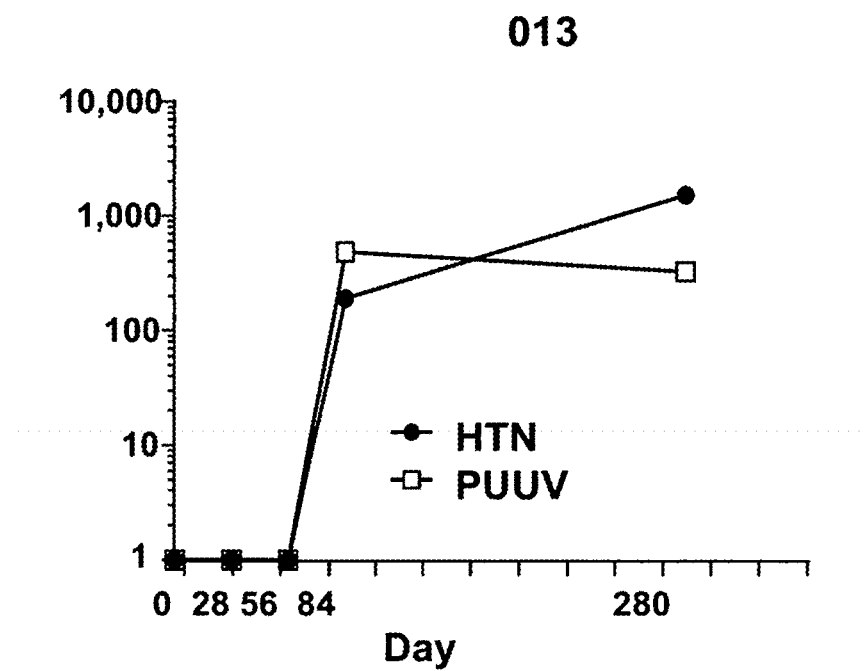
FIG. 15B is a graph showing showing pseudovirion neutralization titers in individual 013 responding to both vaccines.
Figure 15C:
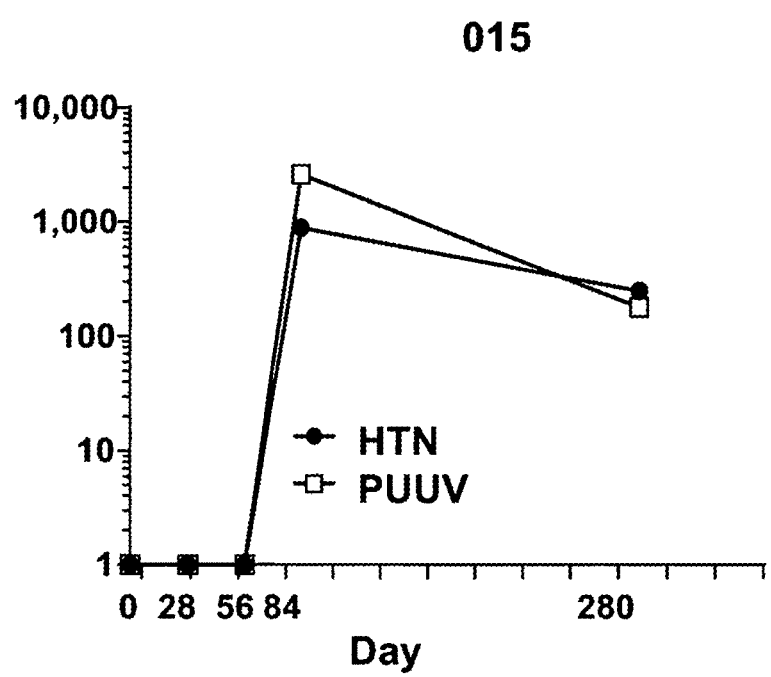
FIG. 15C is a graph showing showing pseudovirion neutralization titers in individual 015 responding to both vaccines.
Figure 15D:
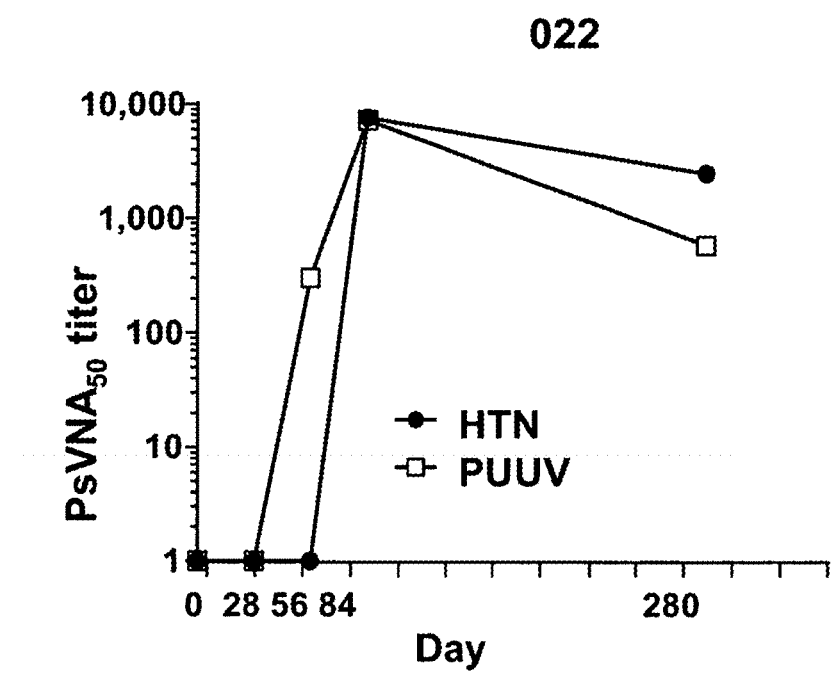
FIG. 15D is a graph showing showing pseudovirion neutralization titers in individual 022 responding to both vaccines.
Figure 15E:
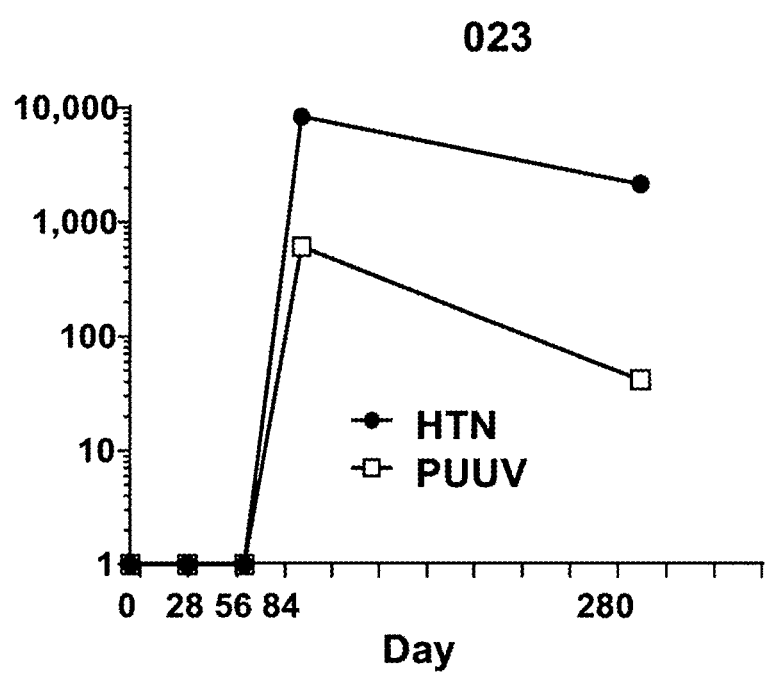
FIG. 15E is a graph showing showing pseudovirion neutralization titers in individual 023 responding to both vaccines.
Figure 15F:
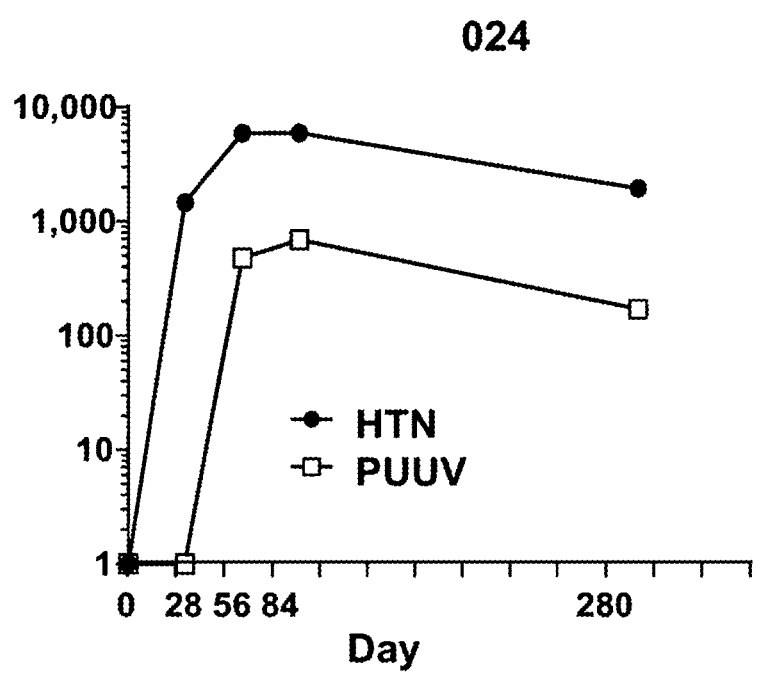
FIG. 15F is a graph showing showing pseudovirion neutralization titers in individual 024 responding to both vaccines.

Optimized HTNV Study in Hamsters Showing that Interference has been Overcome Using the Inventive Optimized HTNV DNA Vaccine FIG. 9 and FIG. 10 demonstrate the immunogenicity of the inventive optimized HTNV DNA vaccine when mixed 1:1 with PUUV DNA vaccine (US 2010/0323024A1) delivered to hamsters by IM-EP in two separate studies. The hamsters were vaccinated three times at 3-4 week intervals by IM-EP with 100 µg of the individual DNAs or with a 1:1 mixture the optimized HTNV and PUUV DNAs (50 µg of each). Geometric mean antibody titers ($GMT_{50}$) for each group of eight hamsters are shown as the reciprocal of the dilution of sera required to reduce plaque counts of controls by 50%. As expected, because half as much of the optimized HTNV DNA was given in the mixture as compared to in those receiving only the optimized HTNV DNA vaccine, the antibody response to HTNV was slightly reduced. Following injection of HTNV into the vaccinated hamsters, it was determined that none of the hamsters vaccinated with the mixed vaccines showed evidence of infection with HTNV (as determined by measuring antibodies to the N protein, which is not part of the vaccine, data not shown). Consequently, the mixed vaccines containing the inventive optimized HTNV DNA vaccine can elicit neutralizing antibodies against HTNV and also protect from infection by HTNV. Moreover, there was no detectable interference observed when the inventive HTNV DNA vaccine was mixed with the PUUV DNA vaccine.

Example 5

Non-Optimized HTNV DNA Vaccine Phase 1 Clinical Study Using IM-EP Delivery, Showing that Mixed HTNV and PUUV DNA Vaccines Result in Reduced Response to HTNV, i.e., Interference FIG. 12 A-D show neutralizing antibody responses of volunteers vaccinated by IM-EP with the individual or mixed non-optimized HTNV and optimized-PUUV DNA vaccines. Seven of eleven volunteers that were vaccinated with the non-optimized HTNV DNA vaccine developed neutralizing antibodies to HTNV. Six of eight volunteers vaccinated with optimized PUUV vaccine developed neutralizing antibodies to PUUV. Three of nine volunteers vaccinated with the combination vaccine developed antibodies to both HTNV and PUUV. However four additional volunteers had antibodies only to PUUV but no additional volunteers had antibodies only to HTNV. Interference, while not complete, is still a problem. These results are in line with the results in Example 2.

Preparation of Optimized DNA Vaccines

The optimized HTNV DNA vaccine was constructed by cloning cDNA representing the optimized HTNV M segment open reading frame, which encodes Gn and Gc, into the NotI and BglII-restriction sites of pWRG7077 [14] as described previously [8]. The PUUV DNA vaccine was previously constructed similarly, using cDNA that was engineered as a consensus sequence of several PUUV strains, and codon-optimized (GeneArt) [15] and (US 2010/0323024A1). The HTNV and PUUV DNA vaccines were produced under current Good Manufacturing Practices (cGMP) by Althea Technologies, Inc. (San Diego, Calif.). A summary of the manufacturing and testing processes that Althea was contracted to perform is as follows: Optimized HTNV DNA vaccine plasmid is manufactured under cGMP specification, to include (a) Establishment and Characterization of a Manufacturer's Master Cell Bank (MCB) (b) Process Optimization & Non-GMP Production of a HTNV plasmid DNA vaccine lot, (c) cGMP Production and Characterization of a bulk HTNV Plasmid DNA (2.6 g) (d) Packaging and Shipment of Cell Banks (2 SHIPMENTS), (e) 6 months Bulk Drug Product Storage. Deliverables requested from Althea are (1) a Master cell bank for HTNV, (2) a pilot lot of HTNV DNA plasmid; (3) one cGMP lot of bulk DNA plasmid stored in IPA (2.6 g); and (4) all documents (e.g., batch records, data records and reports, CoAs, BMF letter of cross reference) as required for submission to FDA. The following specific tasks are performed by Althea for manufacture of a bulk DNA vaccine plasmid for HTNV.

Example 6

Optimized HTNV Vaccine

Figure 13:
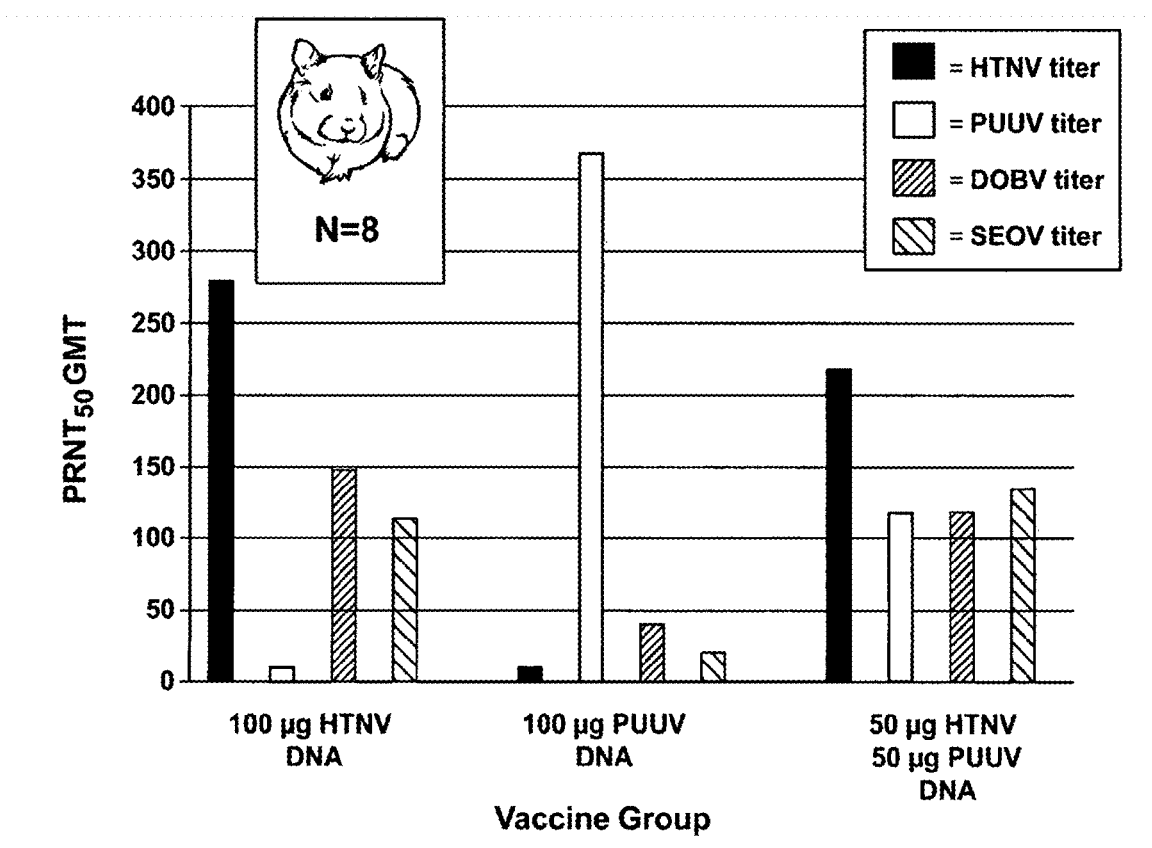

As shown in FIG. 13, gene modifications to overcome interference were made. As previously performed for the PUUV plasmid, the codons of the HTNV plasmid were modified to the bias of *homo sapiens* genes, and known motifs that reduce expression were removed. Hamsters vaccinated with the optimized vaccine of the invention by ID-EP three times at 3-week intervals developed neutralizing antibodies to all four HFRS-causing hantaviruses.

Example 7

FIG. 14 shows a study design for 120 people that receive a mixed optimized vaccine. Two different doses are given (2 mg vs 1 mg) and 2 different schedules with each individual receiving an optional 6-month boost. FIGS. 15a-15f show examples of pseudovirion neutralization titers in various individuals from the study of FIG. 14 responding to both optimized HTNV and PUUV vaccines. Vesicular stomatitis viruses were pseudo typed with optimized HTNV or PUUV glycoproteins and used to assess neutralizing antibody responses of Phase 2a vaccine recipients at indicated days post vaccination. The individuals of FIGS. 15 a-15f are also represented in FIG. 16.

Example 8

Figure 16:
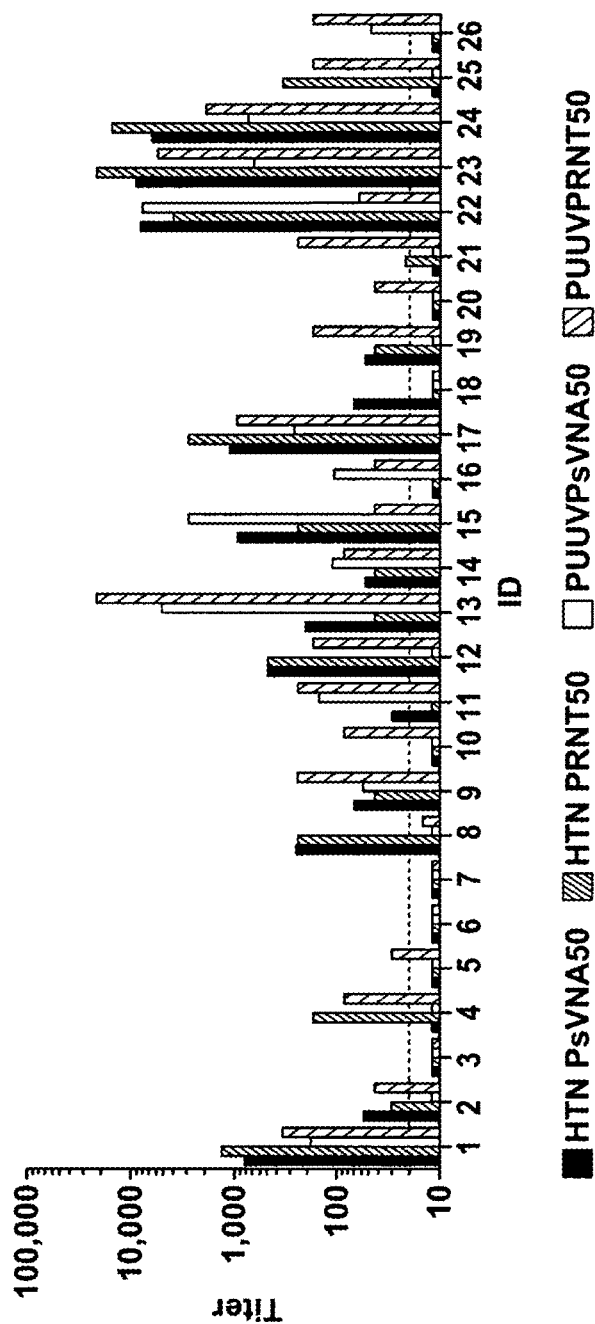
FIG. 16 is a graph showing neutralizing antibody responses in 26 vaccine recipients four weeks after the third vaccination with the mixed optimized HTNV and PUUV DNA vaccine by IM-EP, indicating high antibody responses to both viruses in some individuals.

FIG. 16 also shows results from the study design of FIG. 14. FIG. 16 shows neutralizing antibody responses detected in sera of the first 26 vaccine recipients four weeks after the third vaccination with optimized HTNV and PUUV DNA vaccines by IM-EP. As samples are blinded until completion of this study, it is not possible to assess dose or route factors with these samples. The neutralizing antibody titers were measured using a traditional plaque reduction neutralization test (PRNT) or a vesicular stomatitis virus pseudo typed with the glycoproteins of optimized HTNV or PUUV (Ps-VNA). The bars show each person's neutralizing antibodies to optimized Hantaan or Puumala viruses as measured by the two different tests. The first test uses authentic HTNV (plaque reduction neutralization test) and the second test uses a nonpathogenic virus (VSV) that is coated with HTN proteins (pseudovirion neutralization assay). This second assay can be completed quickly and at BSL2 rather than BSL3 conditions.

Summary:

Phase 1 study results show that DNA vaccines expressing the envelope glycoprotein genes of HTNV and PUUV are safe and immunogenic in humans when delived by IM-EP.

Animal studies suggest that immune interference between the HTNV and PUUV plasmids can be resolved using gene-optimized plasmids. Dose and schedule studies are in progress using the optimized plasmids.

Figure 17:
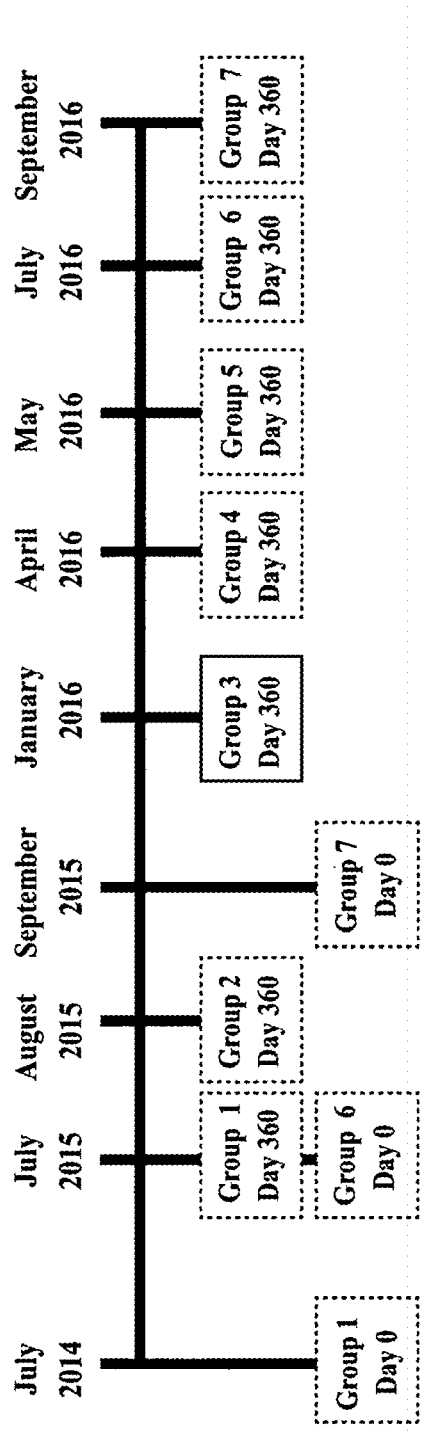
FIG. 17 is a Timeline graph of the Phase 2a study.

Preliminary (blinded) analysis of sera from a subset of Phase 2a time points (FIG. 17) shows that in the first 26 vaccinees, the overall seroconversion rate is 92% with 81% positive for optimized HTNV and 88% positive for PUUV at one or more time points.

Establishment of Master Cell Bank (MCB)
Includes:
    Preparation of MCB batch record
    Transformation
    Selection, genetic stability
    Growth
    Dispensing/freezing (no less than 200 vials)
Characterization of MCB
Includes:
    Completion of MCB testing outlined in Attachment 1
    QA review of associated testing
    Generation of C of A
Non-GMP Production/Process Optimization
Includes:
    Evaluation of plasmid in Althea's fermentation and purification processes
    Non-GMP plasmid will be provided to USAMRMC for research use only
    Appearance, size, and identity of plasmid by restriction analysis using two common enzymes
    Purity by gel electrophoresis
    A260/280 (1.7/2.0)
    Endotoxin by LAL
An optimization study must be completed prior to GMP Production
cGMP Production and Characterization of Plasmid DNA (2.6 g)
Includes:
    Establishment of specifications
    Preparation of customized cGMP Manufacturing Batch Records
    Optimization of fermentation conditions
    Fermentation
    Development of large scale purification process
    Cell lysis
    Downstream processing and separation
    Column purification
    Preparation of standard bulk
    In-process testing
Shipping
Packaging and Shipment of Cell Banks (2SHIPMENTS)
    Includes the management and preparation of the cell banks
    Includes verification of shipment products from Althea to a USAMRMC specified destination
    Includes temperature controlled shipping containers with temperature loggers
    Preparation of all required shipping documentation
Shipping on dry ice
Bulk Drug Product Storage (6 months)
    Includes temperature monitored storage of Bulk Drug Product.

pWRG7077HTN-M-CO
DNA of M segment and plasmid together

SEQ ID NO. 1

GGGGGGGGGGGGCGCTGAGGTCTGCCTCGTGAAGAAGGTGTTGCTGACTC

ATACCAGGCCTGAATCGCCCCATCATCCAGCCAGAAAGTGAGGGAGCCAC

GGTTGATGAGAGCTTTGTTGTAGGTGGACCAGTTGGTGATTTTGAACTTT

TGCTTTGCCACGGAACGGTCTGCGTTGTCGGGAAGATGCGTGATCTGATC

CTTCAACTCAGCAAAAGTTCGATTTATTCAACAAAGCCGCCGTCCCGTCA

AGTCAGCGTAATGCTCTGCCAGTGTTACAACCAATTAACCAATTCTGATT

AGAAAAACTCATCGAGCATCAAATGAAACTGCAATTTATTCATATCAGGA

TTATCAATACCATATTTTTGAAAAAGCCGTTTCTGTAATGAAGGAGAAAA

CTCACCGAGGCAGTTCCATAGGATGGCAAGATCCTGGTATCGGTCTGCGA

TTCCGACTCGTCCAACATCAATACAACCTATTAATTTCCCCTCGTCAAAA

ATAAGGTTATCAAGTGAGAAATCACCATGAGTGACGACTGAATCCGGTGA

GAATGGCAAAAGCTTATGCATTTCTTTCCAGACTTGTTCAACAGGCCAGC

CATTACGCTCGTCATCAAAATCACTCGCATCAACCAAACCGTTATTCATT

CGTGATTGCGCCTGAGCGAGACGAAATACGCGATCGCTGTTAAAAGGACA

ATTACAAACAGGAATCGAATGCAACCGGCGCAGGAACACTGCCAGCGCAT

CAACAATATTTTCACCTGAATCAGGATATTCTTCTAATACCTGGAATGCT

GTTTTCCCGGGGATCGCAGTGGTGAGTAACCATGCATCATCAGGAGTACG

GATAAAATGCTTGATGGTCGGAAGAGGCATAAATTCCGTCAGCCAGTTTA

GTCTGACCATCTCATCTGTAACATCATTGGCAACGCTACCTTTGCCATGT

TTCAGAAACAACTCTGGCGCATCGGGCTTCCCATACAATCGATAGATTGT

CGCACCTGATTGCCCGACATTATCGCGAGCCCATTTATACCCATATAAAT

CAGCATCCATGTTGGAATTTAATCGCGGCCTCGAGCAAGACGTTTCCCGT

TGAATATGGCTCATAACACCCCTTGTATTACTGTTTATGTAAGCAGACAG

TTTTATTGTTCATGATGATATATTTTTATCTTGTGCAATGTAACATCAGA

GATTTTGAGACACAACGTGGCTTTCCCCCCCCCCCGGCATGCCTGCAGG

TCGACAATATTGGCTATTGGCCATTGCATACGTTGTATCTATATCATAAT

ATGTACATTTATATTGGCTCATGTCCAATATGACCGCCATGTTGACATTG

ATTATTGACTAGTTATTAATAGTAATCAATTACGGGGTCATTAGTTCATA

GCCCATATATGGAGTTCCGCGTTACATAACTTACGGTAAATGGCCCGCCT

GGCTGACCGCCCAACGACCCCCGCCCATTGACGTCAATAATGACGTATGT

-continued

TCCCATAGTAACGCCAATAGGGACTTTCCATTGACGTCAATGGGTGGAGT
ATTTACGGTAAACTGCCCACTTGGCAGTACATCAAGTGTATCATATGCCA
AGTCCGCCCCCTATTGACGTCaATGACGGTAAATGGCCCGCCTGGCATTA
TGCCCAGTACATGACCTTACGGGACTTTCCTACTTGGCAGTACATCTACG
TATTAGTCATCGCTATTACCATGGTGATGCGGTTTTGGCAGTACACCAAT
GGGCGTGGATAGCGGTTTGACTCACGGGGATTTCCAAGTCTCCACCCCAT
TGACGTCAATGGGAGTTTGTTTTGGCACCAAAATCAACGGGACTTTCCAA
AATGTCGTAATAACCCCGCCCCGTTGACGCAAATGGGCGGTAGGCGTGTA
CGGTGGGAGGTCTATATAAGCAGAGCTCGTTTAGTGAACCGTCAGATCGC
CTGGAGACGCCATCCACGCTGTTTTGACCTCCATAGAAGACACCGGGACC
GATCCAGCCTCCGCGGCCGGGAACGGTGCATTGGAACGCGGATTCCCCGT
GCCAAGAGTGACGTAAGTACCGCCTATAGACTCTATAGGCACACCCCTTT
GGCTCTTATGCATGCTATACTGTTTTTGGCTTGGGGCCTATACACCCCCG
CTTCCTTATGCTATAGGTGATGGTATAGCTTAGCCTATAGGTGTGGGTTA
TTGACCATTATTGACCACTCCCTATTGGTGACGATACTTTCCATTACTA
ATCCATAACATGGCTCTTTGCCACAACTATCTCTATTGGCTATATGCCAA
TACTCTGTCCTTCAGAGACTGACACGGACTCTGTATTTTTACAGGATGGG
GTCCCATTTATTATTTACAAATTCACATATACAACAACGCCGTCCCCCGT
GCCCGCAGTTTTTATTAAACATAGCGTGGGATCTCCACGCGAATCTCGGG
TACGTGTTCCGGACATGGGCTCTTCTCCGGTAGCGGCGGAGCTTCCACAT
CCGAGCCCTGGTCCCATGCCTCCAGCGGCTCATGGTCGCTCGGCAGCTCC
TTGCTCCTAACAGTGGAGGCCAGACTTAGGCACAGCACAATGCCCACCAC
CACCAGTGTGCCGCACAAGGCCGTGGCGGTAGGGTATGTGTCTGAAAATG
AGCTCGGAGATTGGGCTCGCACCGCTGACGCAGATGGAAGACTTAAGGCA
GCGGCAGAAGAAGATGCAGGCAGCTGAGTTGTTGTATTCTGATAAGAGTC
AGAGGTAACTCCCGTTGCGGTGCTGTTAACGGTGGAGGGCAGTGTAGTCT
GAGCAGTACTCGTTGCTGCCGCGCGCCACCAGACATAATAGCTGACAG
ACTAACAGACTGTTCCTTTCCATGGGTCTTTTCTGCAGTCACCGTCCAAG
CTTGCGGCCGCCACCATGGGCATCTGGAAGTGGCTGGTCATGGCTAGCCT
CGTGTGGCCCGTGCTGACCCTGCGGAACGTGTACGACATGAAGATCGAGT
GCCCCCACACCGTGTCCTTCGGCGAGAACAGCGTGATCGGCTACGTGGAA
CTGCCCCCGTGCCCTGGCCGATACAGCTCAGATGGTGCCCGAGAGCAG
CTGCAGCATGGACAACCACCAGAGCCTGAACACCATCACCAAGTACACCC
AGGTGTCCTGGCGGGGCAAGGCCGATCAGAGCCAGAGCAGCCAGAACAGC
TTCGAGACAGTGTCTACCGAGGTGGACCTGAAGGGCACCTGTGCCCTGAA
GCACAAGATGGTGGAAGAGAGCTACCGGTCCAGAAAGAGCGTGACCTGCT
ACGACCTGAGCTGCAACAGCACCTACTGCAAGCCCACCCTGTACATGATC
GTGCCCATCCACGCCTGCAACATGATGAAGTCCTGCCTGATCGCCCTGGG
CCCCTACAGAGTGCAGGTCGTGTACGAGCGGAGCTACTGCATGACCGGCG
TGCTGATCGAGGGCAAGTGCTTCGTGCCCGACCAGAGCGTGGTGTCCATC
ATCAAGCACGGCATCTTCGATATCGCCAGCGTGCACATCGTGTGCTTTTT

-continued

CGTGGCCGTCAAGGGCAACACCTACAAGATTTTCGAGCAGGTCAAAAAGA
GCTTCGAGAGCACCTGTAACGACACCGAGAACAAGGTGCAGGGCTACTAC
ATCTGCATCGTGGGCGGCAACAGCGCCCCCATCTACGTGCCCACCCTGGA
CGACTTCCGGTCCATGGAAGCTTCACCGGCATCTTCAGAAGCCCCCACG
GCGAGGACCACGACCTGGCCGGCGAGGAAATCGCCAGCTACTCCATCGTG
GGCCCTGCCAACGCCAAGGTGCCACACAGCGCCAGCAGCGACACCCTGTC
CCTGATCGCCTACAGCGGCATCCCCAGCTACAGCAGCCTGAGCATCCTGA
CCAGCAGCACCGAGGCCAAGCACGTGTTCAGCCCTGGCCTGTTCCCCAAG
CTGAACCACACCAACTGCGACAAGAGCGCCATCCCCCTGATCTGGACCGG
CATGATCGACCTGCCCGGCTACTACGAGGCCGTGCACCCCTGCACCGTGT
TCTGCGTGCTGTCTGGCCCTGGAGCCAGCTGCGAGGCCTTTTCTGAGGGC
GGCATCTTTAACATCACCAGCCCCATGTGCCTGGTGTCCAAGCAGAACCG
GTTCCGGCTGACCGAGCAGCAGGTCAACTTCGTGTGCCAGCGGGTGGACA
TGGACATCGTGGTGTACTGCAACGGCCAGCGGAAAGTGATCCTGACCAAG
ACCCTCGTGATCGGCCAGTGCATCTACACCATCACAAGCCTGTTCAGCCT
GCTGCCCGGCGTGGCCCACTCTATCGCCGTGGAACTGTGCGTGCCCGGCT
TTCACGGCTGGGCCACAGCTGCCCTGCTGGTCACCTTCTGCTTCGGCTGG
GTGCTGATCCCCGCCATCACCTTCATCATCCTGACCGTGCTGAAGTTTAT
CGCCAACATCTTCCACACCAGCAACCAGGAAAACCGGCTCAAGTCCGTGC
TGCGGAAGATCAAAGAGGAATTCGAAAAGACCAAGGGCAGCATGGTCTGC
GACGTGTGCAAATACGAGTGCGAGACATACAAAGAGCTGAAGGCCCACGG
CGTGTCCTGCCCTCAGAGCCAGTGCCCCTACTGCTTCACCCACTGCGAGC
CTACCGAGGCCGCCTTCCAGGCCCACTACAAAGTGTGCCAGGTCACACAC
CGGTTCAGGGACGACCTGAAGAAAACCGTGACCCCCCAGAACTTCACCCC
CGGCTGCTACCGGACCCTGAACCTGTTCCGGTACAAGACCGGTGCTACA
TCTTTACCATGTGGATCTTTCTGCTGGTGCTCGAGTCCATCCTGTGGGCC
GCCAGCGCCAGCGAAACCCTCTGACCCCCGTGTGGAACGACAACGCCCA
TGGCGTGGGCTCTGTGCCCATGCACACCGACCTGGAACTGGACTTCAGCC
TGACCAGCTCCAGCAAGTACACCTACCGGCGGAAGCTGACCAACCCCCTG
GAAGAGGCCCAGAGCATCGACCTGCACATCGAGATCGAGGAACAGACCAT
CGGAGTCGATGTCCACGCCCTGGGACATTGGTTCGACGGACGGCTGAACC
TGAAAACCAGCTTCCACTGCTACGGCGCCTGCACTAAGTACGAGTACCCC
TGGCACACCGCCAAGTGCCACTACGAGCGGGACTACCAGTACGAGACAAG
CTGGGGCTGTAACCCCAGCGACTGTCCAGGCGTGGGCACCGGCTGTACAG
CTTGTGGCCTGTACCTGGACCAGCTGAAGCCCGTGGGCTCCGCCTACAAG
ATCATCACCATCCGGTACAGCAGACGCGTGTGCGTGCAGTTCGGCGAAGA
GAACCTGTGCAAGATCATCGACATGAACGACTGCTTCGTGTCCCGGCACG
TGAAAGTGTGCATCATCGGCACCGTGTCCAAGTTCAGCCAGGGCGATACC
CTGCTGTTCTTCGGCCCTCTGGAAGGCGGCGGACTGATCTTCAAGCACTG
GTGCACAAGCACCTGTCAGTTTGGCGACCCCGGCGACATCATGAGCCCCA
GAGACAAGGGCTTCCTGTGCCCCGAGTTCCCCGGCAGCTTCCGGAAGAAG

-continued

TGCAACTTCGCCACCACCCCCATCTGCGAGTACGACGGCAACATGGTGTC

CGGCTACAAGAAAGTGATGGCCACCATCGACAGCTTCCAGAGCTTCAACA

CCTCCACCATGCACTTCACCGACGAGCGGATCGAGTGGAAGGACCCCGAC

GGCATGCTGCGGGACCACATCAACATCCTGGTCACCAAGGACATCGACTT

CGACAACCTGGGCGAGAACCCCTGCAAGATCGGCCTGCAGACCTCCAGCA

TCGAGGGCGCTTGGGGCAGCGGCGTGGGCTTTACCCTGACCTGTCTGGTG

TCCCTGACCGAGTGCCCCACCTTCCTGACCTCCATCAAGGCCTGCGACAA

GGCCATCTGTTACGGCGCCGAGTCCGTGACCCTGACAAGAGGCCAGAACA

CCGTGAAGGTGTCCGGCAAAGGCGGCCACAGCGGCAGCACCTTCAGATGC

TGCCACGGGGAGGACTGCAGCCAGATCGGACTGCATGCCGCAGCACCCCA

CCTGGACAAAGTGAACGGCATCAGCGAGATCGAGAACTCCAAGGTGTACG

ACGATGGCGCCCCTCAGTGCGGCATCAAGTGTTGGTTCGTGAAGTCCGGC

GAGTGGATCAGCGGCATCTTCTCCGGCAACTGGATCGTGCTGATTGTGCT

GTGCGTGTTCCTGCTGTTTAGCCTGGTGCTGCTGAGCATTCTGTGTCCCG

TGCGCAAGCACAAGAAAAGCTGATGAAGATCTACGTATGATCAGCCTCGA

CTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGA

GGAAATTGCATCGCATTGTCTGAGTAGGTGTCATTCTATTCTGGGGGGTG

GGGTGGGGCAGGACAGCAAGGGGGAGGATTGGGAAGACAATAGCAGGCAT

GCTGGGGATGCGGTGGGCTCTATGGCTTCTGAGGCGGAAAGAACCAGCTG

GGGCTCGACAGCTCGACTCTAGaATTGCTTCCTCGCTCACTGACTCGCTG

CGCTCGGTCGTTCGGCTGCGGCGAGCGGTATCAGCTCACTCAAAGGCGGT

AATACGGTTATCCACAGAATCAGGGGATAACGCAGGAAAGAACATGTGAG

CAAAAGGCCAGCAAAAGGCCAGGAACCGTAAAAAGGCCGCGTTGCTGGCG

TTTTTCCATAGGCTCCGCCCCCCTGACGAGCATCACAAAAATCGACGCTC

AAGTCAGAGGTGGCGAAACCCGACAGGACTATAAAGATACCAGGCGTTTC

CCCCTGGAAGCTCCCTCGTGCGCTCTCCTGTTCCGACCCTGCCGCTTACC

GGATACCTGTCCGCCTTTCTCCCTTCGGGAAGCGTGGCGCTTTCTCATAG

CTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGT

AACTATCGTCTTGAGTCCAACCCGGTAAGACACGACTTATCGCCACTGGC

AGCAGCCACTGGTAACAGGATTAGCAGAGCGAGGTATGTAGGCGGTGCTA

CAGAGTTCTTGAAGTGGTGGCCTAACTACGGCTACACTAGAAGAACAGTA

TTTGGTATCTGCGCTCTGCTGAAGCCAGTTACCTTCGGAAAAAGAGTTGG

TAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCT

TTGATCTTTTCTACGGGGTCTGACGCTCAGTGGAACGAAAACTCACGTTA

AGGGATTTTGGTCATGAGATTATCAAAAAGGATCTTCACCTAGATCCTTT

TAAATTAAAAATGAAGTTTTAAATCAATCTAAAGTATATATGAGTAAACT

TGGTCTGACAGTTACCAATGCTTAATCAGTGAGGCACCTATCTCAGCGAT

CTGTCTATTTCGTTCATCCATAGTTGCCTGACTC

-continued

HTN-M-CO
Optimized DNA of M segment

SEQ ID NO. 2

ATGGGCATCTGGAAGTGGCTGGTCATGGCTAGCCTCGTGTGGCCCGTGCT

GACCCTGCGGAACGTGTACGACATGAAGATCGAGTGCCCCCACACCGTGT

CCTTCGGCGAGAACAGCGTGATCGGCTACGTGGAACTGCCCCCCGTGCCC

CTGGCCGATACAGCTCAGATGGTGCCCGAGAGCAGCTGCAGCATGGACAA

CCACCAGAGCCTGAACACCATCACCAAGTACACCCAGGTGTCCTGGCGGG

GCAAGGCCGATCAGAGCCAGAGCAGCCAGAACAGCTTCGAGACAGTGTCT

ACCGAGGTGGACCTGAAGGGCACCTGTGCCCTGAAGCACAAGATGGTGGA

AGAGAGCTACCGGTCCAGAAAGAGCGTGACCTGCTACGACCTGAGCTGCA

ACAGCACCTACTGCAAGCCCACCCTGTACATGATCGTGCCCATCCACGCC

TGCAACATGATGAAGTCCTGCCTGATCGCCCTGGGCCCCTACAGAGTGCA

GGTCGTGTACGAGCGGAGCTACTGCATGACCGGCGTGCTGATCGAGGGCA

AGTGCTTCGTGCCCGACCAGAGCGTGGTGTCCATCATCAAGCACGGCATC

TTCGATATCGCCAGCGTGCACATCGTGTGCTTTTTCGTGGCCGTCAAGGG

CAACACCTACAAGATTTTCGAGCAGGTCAAAAAGAGCTTCGAGAGCACCT

GTAACGACACCGAGAACAAGGTGCAGGGCTACTACATCTGCATCGTGGGC

GGCAACAGCGCCCCCATCTACGTGCCCACCCTGGACGACTTCCGGTCCAT

GGAAGCCTTCACCGGCATCTTCAGAAGCCCCCACGGCGAGGACCACGACC

TGGCCGGCGAGGAAATCGCCAGCTACTCCATCGTGGGCCCTGCCAACGCC

AAGGTGCCACACAGCGCCAGCAGCGACACCCTGTCCCTGATCGCCTACAG

CGGCATCCCCAGCTACAGCAGCCTGAGCATCCTGACCAGCAGCACCGAGG

CCAAGCACGTGTTCAGCCCTGGCCTGTTCCCCAAGCTGAACCACACCAAC

TGCGACAAGAGCGCCATCCCCCTGATCTGGACCGGCATGATCGACCTGCC

CGGCTACTACGAGGCCGTGCACCCCTGCACCGTGTTCTGCGTGCTGTCTG

GCCCTGGAGCCAGCTGCGAGGCCTTTTCTGAGGGCGGCATCTTTAACATC

ACCAGCCCCATGTGCCTGGTGTCCAAGCAGAACCGGTTCCGGCTGACCGA

GCAGCAGGTCAACTTCGTGTGCCAGCGGGTGGACATGGACATCGTGGTGT

ACTGCAACGGCCAGCGGAAAGTGATCCTGACCAAGACCCTCGTGATCGGC

CAGTGCATCTACACCATCACAAGCCTGTTCAGCCTGCTGCCCGGCGTGGC

CCACTCTATCGCCGTGGAACTGTGCGTGCCCGGCTTTCACGGCTGGGCCA

CAGCTGCCCTGCTGGTCACCTTCTGCTTCGGCTGGGTGCTGATCCCCGCC

ATCACCTTCATCATCCTGACCGTGCTGAAGTTTATCGCCAACATCTTCCA

CACCAGCAACCAGGAAAACCGGCTCAAGTCCGTGCTGCGGAAGATCAAAG

AGGAATTCGAAAAGACCAAGGGCAGCATGGTCTGCGACGTGTGCAAATAC

GAGTGCGAGACATACAAAGAGCTGAAGGCCCACGGCGTGTCCTGCCCTCA

GAGCCAGTGCCCCTACTGCTTCACCCACTGCGAGCCTACCGAGGCCGCCT

TCCAGGCCCACTACAAAGTGTGCCAGGTCACACACCGGTTCAGGGACGAC

CTGAAGAAAACCGTGACCCCCCAGAACTTCACCCCCCGGCTGCTACCGGAC

CCTGAACCTGTTCCGGTACAAGAGCCGGTGCTACATCTTTACCATGTGGA

TCTTTCTGCTGGTGCTCGAGTCCATCCTGTGGGCCGCCAGCGCCAGCGAA

```
ACCCCTCTGACCCCCGTGTGGAACGACAACGCCCATGGCGTGGGCTCTGT
GCCCATGCACACCGACCTGGAACTGGACTTCAGCCTGACCAGCTCCAGCA
AGTACACCTACCGGCGGAAGCTGACCAACCCCCTGGAAGAGGCCCAGAGC
ATCGACCTGCACATCGAGATCGAGGAACAGACCATCGGAGTCGATGTCCA
CGCCCTGGGACATTGGTTCGACGGACGGCTGAACCTGAAAACCAGCTTCC
ACTGCTACGGCGCCTGCACTAAGTACGAGTACCCCTGGCACACCGCCAAG
TGCCACTACGAGCGGGACTACCAGTACGAGACAAGCTGGGCTGTAACCC
CAGCGACTGTCCAGGCGTGGGCACCGGCTGTACAGCTTGTGGCCTGTACC
TGGACCAGCTGAAGCCCGTGGGCTCCGCCTACAAGATCATCACCATCCGG
TACAGCAGACGCGTGTGCGTGCAGTTCGGCGAAGAGAACCTGTGCAAGAT
CATCGACATGAACGACTGCTTCGTGTCCCGGCACGTGAAAGTGTGCATCA
TCGGCACCGTGTCCAAGTTCAGCCAGGGCGATACCCTGCTGTTCTTCGGC
CCTCTGGAAGGCGGCGGACTGATCTTCAAGCACTGGTGCACAAGCACCTG
TCAGTTTGGCGACCCCGGCGACATCATGAGCCCCAGAGACAAGGGCTTCC
TGTGCCCCGAGTTCCCCGGCAGCTTCCGGAAGAAGTGCAACTTCGCCACC
ACCCCCATCTGCGAGTACGACGGCAACATGGTGTCCGGCTACAAGAAAGT
GATGGCCACCATCGACAGCTTCCAGAGCTTCAACACCTCCACCATGCACT
TCACCGACGAGCGGATCGAGTGGAAGGACCCCGACGGCATGCTGCGGGAC
CACATCAACATCCTGGTCACCAAGGACATCGACTTCGACAACCTGGGCGA
GAACCCCTGCAAGATCGGCCTGCAGACCTCCAGCATCGAGGGCGCTTGGG
GCAGCGGCGTGGGCTTTACCCTGACCTGTCTGGTGTCCCTGACCGAGTGC
CCCACCTTCCTGACCTCCATCAAGGCCTGCGACAAGGCCATCTGTTACGG
CGCCGAGTCCGTGACCCTGACAAGAGGCCAGAACACCGTGAAGGTGTCCG
GCAAAGGCGGCCACAGCGGCAGCACCTTCAGATGCTGCCACGGGGAGGAC
TGCAGCCAGATCGGACTGCATGCCGCAGCACCCCACCTGGACAAAGTGAA
CGGCATCAGCGAGATCGAGAACTCCAAGGTGTACGACGATGGCGCCCCTC
AGTGCGGCATCAAGTGTTGGTTCGTGAAGTCCGGCGAGTGGATCAGCGGC
ATCTTCTCCGGCAACTGGATCGTGCTGATTGTGCTGTGCGTGTTCCTGCT
GTTTAGCCTGGTGCTGCTGAGCATTCTGTGTCCCGTGCGCAAGCACAAGA
AAAGCTGATGA
``` pWRG7077
plasmid

SEQ ID NO. 3

```
GGGGGGGGGGGGCGCTGAGGTCTGCCTCGTGAAGAAGGTGTTGCTGACTC
ATACCAGGCCTGAATCGCCCCATCATCCAGCCAGAAAGTGAGGGAGCCAC
GGTTGATGAGAGCTTTGTTGTAGGTGGACCAGTTGGTGATTTTGAACTTT
TGCTTTGCCACGGAACGGTCTGCGTTGTCGGGAAGATGCGTGATCTGATC
CTTCAACTCAGCAAAAGTTCGATTTATTCAACAAAGCCGCCGTCCCGTCA
AGTCAGCGTAATGCTCTGCCAGTGTTACAACCAATTAACCAATTCTGATT
AGAAAAACTCATCGAGCATCAAATGAAACTGCAATTTATTCATATCAGGA
TTATCAATACCATATTTTTGAAAAAGCCGTTTCTGTAATGAAGGAGAAAA
CTCACCGAGGCAGTTCCATAGGATGGCAAGATCCTGGTATCGGTCTGCGA
TTCCGACTCGTCCAACATCAATACAACCTATTAATTTCCCCTCGTCAAAA
ATAAGGTTATCAAGTGAGAAATCACCATGAGTGACGACTGAATCCGGTGA
GAATGGCAAAGCTTATGCATTTCTTTCCAGACTTGTTCAACAGGCCAGC
CATTACGCTCGTCATCAAAATCACTCGCATCAACCAAACCGTTATTCATT
CGTGATTGCGCCTGAGCGAGACGAAATACGCGATCGCTGTTAAAAGGACA
ATTACAAACAGGAATCGAATGCAACCGGCGCAGGAACACTGCCAGCGCAT
CAACAATATTTTCACCTGAATCAGGATATTCTTCTAATACCTGGAATGCT
GTTTTCCCGGGGATCGCAGTGGTGAGTAACCATGCATCATCAGGAGTACG
GATAAATGCTTGATGGTCGGAAGAGGCATAAATTCCGTCAGCCAGTTTA
GTCTGACCATCTCATCTGTAACATCATTGGCAACGCTACCTTTGCCATGT
TTCAGAAACAACTCTGGCGCATCGGGCTTCCCATACAATCGATAGATTGT
CGCACCTGATTGCCCGACATTATCGCGAGCCCATTTATACCCATATAAAT
CAGCATCCATGTTGGAATTTAATCGCGGCCTCGAGCAAGACGTTTCCCGT
TGAATATGGCTCATAACACCCCTTGTATTACTGTTTATGTAAGCAGACAG
TTTTATTGTTCATGATGATATATTTTTATCTTGTGCAATGTAACATCAGA
GATTTTGAGACACAACGTGGCTTTCCCCCCCCCCCGGCATGCCTGCAGG
TCGACAATATTGGCTATTGGCCATTGCATACGTTGTATCTATATCATAAT
ATGTACATTTATATTGGCTCATGTCCAATATGACCGCCATGTTGACATTG
ATTATTGACTAGTTATTAATAGTAATCAATTACGGGGTCATTAGTTCATA
GCCCATATATGGAGTTCCGCGTTACATAACTTACGGTAAATGGCCCGCCT
GGCTGACCGCCCAACGACCCCCGCCCATTGACGTCAATAATGACGTATGT
TCCCATAGTAACGCCAATAGGGACTTTCCATTGACGTCAATGGGTGGAGT
ATTTACGGTAAACTGCCCACTTGGCAGTACATCAAGTGTATCATATGCCA
AGTCCGCCCCCTATTGACGTCaATGACGGTAAATGGCCCGCCTGGCATTA
TGCCCAGTACATGACCTTACGGGACTTTCCTACTTGGCAGTACATCTACG
TATTAGTCATCGCTATTACCATGGTGATGCGGTTTTGGCAGTACACCAAT
GGGCGTGGATAGCGGTTTGACTCACGGGGATTTCCAAGTCTCCACCCCAT
TGACGTCAATGGGAGTTTGTTTTGGCACCAAAATCAACGGGACTTTCCAA
AATGTCGTAATAACCCCGCCCCGTTGACGCAAATGGGCGGTAGGCGTGTA
CGGTGGGAGGTCTATATAAGCAGAGCTCGTTTAGTGAACCGTCAGATCGC
CTGGAGACGCCATCCACGCTGTTTTGACCTCCATAGAAGACACCGGGACC
GATCCAGCCTCCGCGGCCGGGAACGGTGCATTGGAACGCGGATTCCCCGT
GCCAAGAGTGACGTAAGTACCGCCTATAGACTCTATAGGCACACCCCTTT
GGCTCTTATGCATGCTATACTGTTTTTGGCTTGGGGCCTATACACCCCCG
CTTCCTTATGCTATAGGTGATGGTATAGCTTAGCCTATAGGTGTGGGTTA
TTGACCATTATTGACCACTCCCCTATTGGTGACGATACTTTCCATTACTA
ATCCATAACATGGCTCTTTGCCACAACTATCTCTATTGGCTATATGCCAA
TACTCTGTCCTTCAGAGACTGACACGGACTCTGTATTTTTACAGGATGGG
GTCCCATTTATTTATTTACAAATTCACATATACAACAACGCCGTCCCCGT
GCCCGCAGTTTTTATTAAACATAGCGTGGGATCTCCACGCGAATCTCGGG
TACGTGTTCCGGACATGGGCTCTTCTCCGGTAGCGGCGGAGCTTCCACAT
```

-continued

```
CCGAGCCCTGGTCCCATGCCTCCAGCGGCTCATGGTCGCTCGGCAGCTCC

TTGCTCCTAACAGTGGAGGCCAGACTTAGGCACAGCACAATGCCCACCAC

CACCAGTGTGCCGCACAAGGCCGTGGCGGTAGGGTATGTGTCTGAAAATG

AGCTCGGAGATTGGGCTCGCACCGCTGACGCAGATGGAAGACTTAAGGCA

GCGGCAGAAGAAGATGCAGGCAGCTGAGTTGTTGTATTCTGATAAGAGTC

AGAGGTAACTCCCGTTGCGGTGCTGTTAACGGTGGAGGGCAGTGTAGTCT

GAGCAGTACTCGTTGCTGCCGCGCGCGCCACCAGACATAATAGCTGACAG

ACTAACAGACTGTTCCTTTCCATGGGTCTTTTCTGCAGTCACCGTCCAAG

CTTGCGGCCGCCACCAGATCTACGTATGATCAGCCTCGACTGTGCCTTCT

AGTTGCCAGCCATCTGTTGTTTGCCCCTCCCCCGTGCCTTCCTTGACCCT

GGAAGGTGCCACTCCCACTGTCCTTTCCTAATAAAATGAGGAAATTGCAT

CGCATTGTCTGAGTAGGTGTCATTCTATTCTGGGGGGTGGGGTGGGGCAG

GACAGCAAGGGGAGGATTGGGAAGACAATAGCAGGCATGCTGGGGATGC

GGTGGGCTCTATGGCTTCTGAGGCGGAAAGAACCAGCTGGGGCTCGACAG

CTCGACTCTAGaATTGCTTCCTCGCTCACTGACTCGCTGCGCTCGGTCGT

TCGGCTGCGGCGAGCGGTATCAGCTCACTCAAAGGCGGTAATACGGTTAT

CCACAGAATCAGGGGATAACGCAGGAAAGAACATGTGAGCAAAAGGCCAG

CAAAAGGCCAGGAACCGTAAAAAGGCCGCGTTGCTGGCGTTTTTCCATAG

GCTCCGCCCCCTGACGAGCATCACAAAAATCGACGCTCAAGTCAGAGGT

GGCGAAACCCGACAGGACTATAAAGATACCAGGCGTTTCCCCCTGGAAGC

TCCCTCGTGCGCTCTCCTGTTCCGACCCTGCCGCTTACCGGATACCTGTC

CGCCTTTCTCCCTTCGGGAAGCGTGGCGCTTTCTCATAGCTCACGCTGTA

GGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCT

TGAGTCCAACCCGGTAAGACACGACTTATCGCCACTGGCAGCAGCCACTG

GTAACAGGATTAGCAGAGCGAGGTATGTAGGCGGTGCTACAGAGTTCTTG

AAGTGGTGGCCTAACTACGGCTACACTAGAAGAACAGTATTTGGTATCTG

CGCTCTGCTGAAGCCAGTTACCTTCGGAAAAAGAGTTGGTAGCTCTTGAT

CCGGCAAACAAACCACCGCTGGTAGCGGTGGTTTTTTTGTTTGCAAGCAG

CAGATTACGCGCAGAAAAAAAGGATCTCAAGAAGATCCTTTGATCTTTTC

TACGGGGTCTGACGCTCAGTGGAACGAAAACTCACGTTAAGGGATTTTGG

TCATGAGATTATCAAAAAGGATCTTCACCTAGATCCTTTTAAATTAAAAA

TGAAGTTTTAAATCAATCTAAAGTATATATGAGTAAACTTGGTCTGACAG

TTACCAATGCTTAATCAGTGAGGCACCTATCTCAGCGATCTGTCTATTTC

GTTCATCCATAGTTGCCTGACTC
```

Bgl II cloning site
SEQ ID NO. 4
AGATCT

Not I cloning site
SEQ ID NO. 5
GCGGCCGC

REFERENCES

1. Hooper J W, Li D. Vaccines against hantaviruses. Curr Top Microbiol Immunol 2001; 256:171-91.
2. Maes P, Clement J, Van Ranst M. Recent approaches in *hantavirus* vaccine development. Expert Rev Vaccines 2009; 8(January (1)):67-76.
3. Wang Q, Zhou H, Han Y H, Wang X F, Wang S W, Yin W W, et al. Epidemiol-ogy and surveillance programs on hemorrhagic fever with renal syndrome in Mainland China, 2005-2008. Zhonghua Liu Xing Bing Xue Za Zhi 2010; 31(June(6)):675-80.
4. Fang L Q, Wang X J, Liang S, Li Y L, Song S X, Zhang W Y, et al. Spatiotemporal trends and climatic factors of hemorrhagic fever with renal syndrome epidemicin Shandong Province, China. PLoS Negl Trop Dis 2010; 4(8): e789.
5. Zhang Y Z, Zou Y, Fu Z F, Plyusnin A. *Hantavirus* infections in humans and animals, China. Emerg Infect Dis August 2010; 16(August (8)):1195-203.
6. Heyman P, Vaheri A. Situation of *hantavirus* infections and haemorrhagic fever with renal syndrome in European countries as of December 2006. Euro Surveil 12008; 13(July (28)).
7. Chu Y K, Jennings G B, Schmaljohn C S. A vaccinia virus-vectored Hantaan virus vaccine protects hamsters from challenge with Hantaan and Seoul viruses but not Puumala virus. J Virol 1995; 69(October (10)):6417-23.
8. Hooper J W, Custer D M, Thompson E, Schmaljohn C S. DNA vaccination with the Hantaan virus M gene protects hamsters against three of four HFRS han-ta viruses and elicits a high-titer neutralizing antibody response in Rhesus monkeys. J Virol 2001; 75(September (18)):8469-77.
9. McClain D J, Summers P L, Harrison S A, Schmaljohn A L, Schmaljohn C S. Clinical evaluation of a vaccinia-vectored Hantaan virus vaccine. J Med Virol 2000; 60(January (1)):77-85.
10. Schmaljohn C S, Hasty S E, Dalrymple J M. Preparation of candidate vaccinia-vectored vaccines for haemorrhagic fever with renal syndrome. Vaccine 1992; 10(1): 10-3.
11. Schmaljohn C S, Chu Y K, Schmaljohn A L, Dalrymple J M. Antigenic subunits of Hantaan virus expressed by baculovirus and vaccinia virus recombinants. J Virol 1990; 64(July (7)):3162-70.
12. Custer D M, Thompson E, Schmaljohn C S, Ksiazek T G, Hooper J W. Active and passive vaccination against *hantavirus* pulmonary syndrome with Andesvirus M genome segment-based DNA vaccine. J Virol 2003; 77(September(18)):9894-905.
13. Hooper J W, Kamrud K I, Elgh F, Custer D, Schmaljohn C S. DNA vaccination with *hantavirus* M segment elicits neutralizing antibodies and protects against Seoul virus infection. Virology 1999; 255(March (2)):269-78.
14. Schmaljohn C, Vanderzanden L, Bray M, Custer D, Meyer B, Li D, et al. Naked DNAvaccines expressing the prM and E genes of Russian spring summer encephalitis virus and Central European encephalitis virus protect mice from homologous and heterologous challenge. J Virol 1997; 71(December (12)):9563-9.
15. Hooper J W, inventor; United States of America, assignee. Puumala Virus Full-Length M Segment-Based DNA Vaccine. United States Patent Application US20100323024, 2010 December 23.
16. Roy M J, Wu M S, Barr L J, Fuller J T, Tussey L G, Speller S, et al. Induction of antigen-specific CD8+ T cells, T helper cells, and protective levels of antibody in humans by particle-mediated administration of a hepatitis B virus DNA vaccine. Vaccine 2000; 19(November (7-8)):764-78.
17. Roberts L K, Barr L J, Fuller D H, McMahon C W, Leese P T, Jones S. Clinical safety and efficacy of a powdered hepatitis B nucleic acid vaccine delivered to the epidermis by a commercial prototype device. Vaccine 2005; 23(September(40)):4867-78.
18. Badger C V, Richardson J D, Dasilva R L, Richards M J, Josleyn M D, Dupuy L C, et al. Development and application of a flow cytometric potency assay for DNA vaccines. Vaccine 2011; (January):6728-35.
19. Rossi C A, Ksiazek T G. Enzyme-linked immunoborbent assay (ELISA). In: Lee H W, Calisher C, Schmaljohn C, editors. Manual of hemorrhagic fever with renal k syndrome and *hantavirus* pulmonary syndrome. Seoul, Korea: WHO Collabo-rating Center for Virus Reference and Research (Hantaviruses), Asan Institute for Life Sciences; 1999. p. 87-98.
20. Schmaljohn C S, Hasty S E, Dalrymple J M, LeDuc J W, Lee H W, von Bonsdorff C H, et al. Antigenic and genetic properties of viruses linked to hemorrhagic fever with renal syndrome. Science 1985; 227(March (4690)):1041-4.
21. Chu Y K, Jennings G, Schmaljohn A, Elgh F, Hjelle B, Lee H W, et al. Cross-neutralization of hantaviruses with immune sera from experimentally infected animals and from hemorrhagic fever with renal syndrome and *hantavirus* pulmonary syndrome patients. J Infect Dis 1995; 172(December (6)):1581-4.
22. Chu Y K, *Rossi* C, Leduc J W, Lee H W, Schmaljohn C S, Dalrymple J M. Serologi-cal relationships among viruses in the *Hantavirus* genus, family Bunyaviridae. Virology 1994; 198(January (1)):196-204.
23. Fuller D H, Loudon P, Schmaljohn C. Preclinical and clinical progress of particle-mediated DNA vaccines for infectious diseases. Methods 2006; 40(September(1)):86-97.
24. Hooper J W, Custer D M, Smith J, Wahl-Jensen V. Hantaan/Andes virus DNA vaccine elicits a broadly cross-reactive neutralizing antibody response in non-human primates. Virology 2006; 347(March (1)):208-16.
25. Spik K W, Badger C, Mathiessen I, Tjelle T, Hooper J W, Schmaljohn C. Mixing of M segment DNA vaccines to Hantaan virus and Puumala virus reduces their immunogenicity in hamsters. Vaccine 2008; 26(September (40)): 5177-81.
26. Sheshberadaran H, Niklasson B, Tkachenko E A. Antigenic relationship between hantaviruses analysed by immunoprecipitation. J Gen Virol 1988; 69(March (Pt10)):2645-51.
27. Arikawa J, Schmaljohn A L, Dalrymple J M, Schmaljohn C S. Characterization of Hantaan virus envelope glycoprotein antigenic determinants defined by monoclonal antibodies. J Gen Virol 1989; 70(March (Pt 3)):615-24.
28. Che Yk, et al., A vaccine virus-vectored Hantaan virus vaccine protects hamsters from challenge with Hantaan and Seoul viruses but not Puumala virus. J. Virol 1995 October; 69 (10):6417-23.
29. Hooper et al, DNA vaccination with the Hantaan virus M gene protects Hamsters against three of four HFRS hantaviruses and elicits a high-titer neutralizing antibody response in Rhesus monkeys. J Virol 2001, September; 75(18):8469-77.
30. Schmaljohn, et al., Naked DNA vaccines expressing the preM and E genes of Russian spring summer encephalitis virus and Central European encephalitis virus protect mice from homologous and heterologous challenge. J Virol 1997 December; 71(12):9563-9.
31. Spik, et al., Mixing of immunogenicity in hamsters. Vaccine 2008 Sep. 19; 26(40):5177-81.
32. Brocato, R. L., M. J. Josleyn, et al. (2013). "Construction and nonclinical testing of a puumala virus synthetic m gene-based DNA vaccine." Clin Vaccine Immunol 20(2): 218-226.

What is claimed is:

1. A synthetic nucleic acid comprising SEQ ID NO: 1.

2. An immunogenic composition comprising SEQ ID NO: 1.

3. A vector comprising SEQ ID NO: 1.

4. The vector of claim 3, wherein said vector is a plasmid that comprises SEQ ID NO: 1.

5. The plasmid of claim 4, wherein said plasmid comprises pWRG7077.

6. A synthetic DNA construct comprising SEQ ID NO: 2.

7. An immunogenic composition comprising SEQ ID NO: 1, wherein the composition is in or on a carrier.

8. A pharmaceutical formulation comprising the synthetic DNA construct of claim 6 in a pharmaceutically acceptable carrier.

9. The pharmaceutical formulation of claim 8, wherein said synthetic DNA construct is administered on gold particles.

10. A peptide encoded by the nucleic acid sequence of claim 1.

11. A recombinant DNA construct comprising a vector and SEQ ID NO: 2.

12. The recombinant DNA construct of claim 11, wherein said construct is pWRG7077.

13. The recombinant DNA construct of claim 11, which further comprises a promotor functional in a mammal.

14. The recombinant DNA construct of claim 11, wherein the vector is an expression vector.

15. An immunogenic composition comprising inert particles and SEQ ID NO: 1 coated onto said particles.

16. The immunogenic composition of claim 13, wherein said inert particles are gold particles.

17. A synthetic, codon optimized HTNV full length M gene open reading frame of SEQ ID NO: 1.

18. The synthetic nucleic acid of claim 1, encapsulated in nanoparticles.

* * * * *

SEQUENCE LISTING

```
<160> NUMBER OF SEQ ID NOS: 5

<210> SEQ ID NO 1
<211> LENGTH: 7634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gggggggggg ggcgctgagg tctgcctcgt gaagaaggtg ttgctgactc ataccaggcc      60
tgaatcgccc catcatccag ccagaaagtg agggagccac ggttgatgag agctttgttg     120
taggtggacc agttggtgat tttgaacttt tgctttgcca cggaacggtc tgcgttgtcg     180
ggaagatgcg tgatctgatc cttcaactca gcaaaagttc gatttattca acaaagccgc     240
cgtcccgtca agtcagcgta atgctctgcc agtgttacaa ccaattaacc aattctgatt     300
agaaaaactc atcgagcatc aaatgaaact gcaatttatt catatcagga ttatcaatac     360 catattttg aaaaagccgt ttctgtaatg aaggagaaaa ctcaccgagg cagttccata     420
ggatggcaag atcctggtat cggtctgcga ttccgactcg tccaacatca atacaaccta     480
ttaatttccc ctcgtcaaaa ataaggttat caagtgagaa atcaccatga gtgacgactg     540
```

-continued

```
aatccggtga gaatggcaaa agcttatgca tttctttcca gacttgttca acaggccagc    600
cattacgctc gtcatcaaaa tcactcgcat caaccaaacc gttattcatt cgtgattgcg    660
cctgagcgag acgaaatacg cgatcgctgt aaaaggaca attacaaaca ggaatcgaat     720
gcaaccggcg caggaacact gccagcgcat caacaatatt ttcacctgaa tcaggatatt    780
cttctaatac ctggaatgct gttttccgg ggatcgcagt ggtgagtaac catgcatcat     840
caggagtacg gataaaatgc ttgatggtcg gaagaggcat aaattccgtc agccagttta    900
gtctgaccat ctcatctgta acatcattgg caacgctacc tttgccatgt ttcagaaaca    960
actctggcgc atcgggcttc ccatacaatc gatagattgt cgcacctgat tgcccgacat   1020
tatcgcgagc ccatttatac ccatataaat cagcatccat gttggaattt aatcgcggcc   1080
tcgagcaaga cgtttcccgt tgaatatggc tcataacacc ccttgtatta ctgtttatgt   1140
aagcagacag ttttattgtt catgatgata tattttatc ttgtgcaatg taacatcaga    1200
gattttgaga cacaacgtgg ctttcccccc cccccggca tgcctgcagg tcgacaatat    1260
tggctattgg ccattgcata cgttgtatct atatcataat atgtacattt atattggctc   1320
atgtccaata tgaccgccat gttgacattg attattgact agttattaat agtaatcaat   1380
tacgggtca ttagttcata gcccatatat ggagttccgc gttacataac ttacggtaaa    1440
tggcccgcct ggctgaccgc ccaacgaccc ccgcccattg acgtcaataa tgacgtatgt   1500
tcccatagta acgccaatag ggactttcca ttgacgtcaa tgggtggagt atttacggta   1560
aactgcccac ttggcagtac atcaagtgta tcatatgcca agtccgcccc ctattgacgt   1620
caatgacggt aaatggcccg cctggcatta tgcccagtac atgaccttac gggactttcc   1680
tacttggcag tacatctacg tattagtcat cgctattacc atggtgatgc ggttttggca   1740
gtacaccaat gggcgtggat agcggtttga ctcacgggga tttccaagtc tccacccat    1800
tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
ccatagaaga caccgggacc gatccagcct ccgcggccgg gaacggtgca ttggaacgcg   2040
gattccccgt gccaagagtg acgtaagtac cgcctataga ctctataggc acacccttt   2100
ggctcttatg catgctatac tgtttttggc ttggggccta tacaccccg cttccttatg    2160
ctataggtga tggtatagct tagcctatag gtgtgggtta ttgaccatta ttgaccactc   2220
ccctattggt gacgatactt tccattacta atccataaca tggctctttg ccacaactat   2280
ctctattggc tatatgccaa tactctgtcc ttcagagact gacacggact ctgtattttt   2340
acaggatggg gtcccattta ttatttacaa attcacatat acaacaacgc cgtccccgt    2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
tctgaaaatg agctcggaga ttgggctcgc accgctgacg cagatggaag acttaaggca   2700
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg ccaccatggg catctggaag tggctggtca   2940
```

-continued

```
tggctagcct cgtgtggccc gtgctgaccc tgcggaacgt gtacgacatg aagatcgagt    3000
gcccccacac cgtgtccttc ggcgagaaca gcgtgatcgg ctacgtggaa ctgcccccg     3060 tgcccctggc cgatacagct cagatggtgc ccgagagcag ctgcagcatg acaaccacc     3120 agagcctgaa caccatcacc aagtacaccc aggtgtcctg gcggggcaag gccgatcaga    3180
gccagagcag ccagaacagc ttcgagacag tgtctaccga ggtggacctg aagggcacct    3240
gtgccctgaa gcacaagatg gtggaagaga gctaccggtc cagaaagagc gtgacctgct    3300
acgacctgag ctgcaacagc acctactgca agcccaccct gtacatgatc gtgcccatcc    3360
acgcctgcaa catgatgaag tcctgcctga tcgccctggg ccctacaga gtgcaggtcg     3420 tgtacgagcg gagctactgc atgaccggcg tgctgatcga gggcaagtgc ttcgtgcccg    3480
accagagcgt ggtgtccatc atcaagcacg gcatcttcga tatcgccagc gtgcacatcg    3540
tgtgcttttt cgtggccgtc aagggcaaca cctacaagat tttcgagcag gtcaaaaaga    3600
gcttcgagag cacctgtaac gacaccgaga caaggtgca gggctactac atctgcatcg     3660
tgggcggcaa cagcgccccc atctacgtgc ccaccctgga cgacttccgg tccatggaag    3720
ccttcaccgg catcttcaga agcccccacg gcgaggacca cgacctggcc ggcgaggaaa    3780
tcgccagcta ctccatcgtg ggccctgcca acgccaaggt gccacacagc gccagcagcg    3840
acaccctgtc cctgatcgcc tacagcggca tccccagcta cagcagcctg agcatcctga    3900
ccagcagcac cgaggccaag cacgtgttca gccctggcct gttccccaag ctgaaccaca    3960
ccaactgcga caagagcgcc atccccctga tctggaccgg catgatcgac ctgcccggct    4020
actacgaggc cgtgcacccc tgcaccgtgt ctgcgtgct gtctggccct ggagccagct      4080
gcgaggcctt ttctgagggc ggcatcttta acatcaccag ccccatgtgc ctggtgtcca    4140
agcagaaccg gttccggctg accgagcagc aggtcaactt cgtgtgccag cgggtggaca    4200
tggacatcgt ggtgtactgc aacggccagc ggaaagtgat cctgaccaag accctcgtga    4260
tcggccagtg catctacacc atcacaagcc tgttcagcct gctgcccggc gtggcccact    4320
ctatcgccgt ggaactgtgc gtgcccggct tcacggctg gccacagct gccctgctgg      4380 tcaccttctg cttcggctgg gtgctgatcc ccgccatcac cttcatcatc ctgaccgtgc    4440
tgaagtttat cgccaacatc ttccacacca gcaaccagga aaaccggctc aagtccgtgc    4500
tgcggaagat caaagaggaa ttcgaaaaga ccaagggcag catggtctgc gacgtgtgca    4560
aatacgagtg cgagacatac aaagagctga aggcccacgg cgtgtcctgc ctcagagcc     4620 agtgcccta ctgcttcacc cactgcgagc ctaccgaggc cgccttccag gcccactaca     4680
aagtgtgcca ggtcacacac cggttcaggg acgacctgaa gaaaaccgtg acccccaga     4740 acttcaccccc cggctgctac cggacccctga acctgttccg gtacaagagc cggtgctaca   4800
tctttaccat gtggatcttt ctgctggtgc tcgagtccat cctgtgggcc gccagcgcca    4860
gcgaaacccc tctgacccc gtgtggaacg acaacgccca tggcgtgggc tctgtgccca     4920
tgcacaccga cctggaactg gacttcagcc tgaccagctc cagcaagtac acctaccggc    4980
ggaagctgac caacccctg gaagaggccc agagcatcga cctgcacatc gagatcgagg     5040
aacagaccat cggagtcgat gtccacgccc tgggacattg gttcgacgga cggctgaacc    5100
tgaaaaccag cttccactgc tacggcgcct gcactaagta cgagtacccc tggcacaccg    5160
ccaagtgcca ctacgagcgg gactaccagt acgagacaag ctgggctgt aaccccagcg     5220 actgtccagg cgtgggcacc ggctgtacag cttgtggcct gtacctggac cagctgaagc    5280
ccgtgggctc cgcctacaag atcatcacca tccggtacag cagacgcgtg tgcgtgcagt    5340
```

```
tcggcgaaga gaacctgtgc aagatcatcg acatgaacga ctgcttcgtg tcccggcacg    5400
tgaaagtgtg catcatcggc accgtgtcca agttcagcca gggcgatacc ctgctgttct    5460
tcggccctct ggaaggcggc ggactgatct tcaagcactg gtgcacaagc acctgtcagt    5520
ttggcgaccc cggcgacatc atgagcccca gagacaaggg cttcctgtgc cccgagttcc    5580
ccggcagctt ccggaagaag tgcaacttcg ccaccacccc catctgcgag tacgacggca    5640
acatggtgtc cggctacaag aaagtgatgg ccaccatcga cagcttccag agcttcaaca    5700
cctccaccat gcacttcacc gacgagcgga tcgagtggaa ggaccccgac ggcatgctgc    5760
gggaccacat caacatcctg gtcaccaagg acatcgactt cgacaacctg ggcgagaacc    5820
cctgcaagat cggcctgcag acctccagca tcgagggcgc ttggggcagc ggcgtgggct    5880
ttaccctgac ctgtctggtg tccctgaccg agtgccccac cttcctgacc tccatcaagg    5940
cctgcgacaa ggccatctgt tacggcgccg agtccgtgac cctgacaaga ggccagaaca    6000
ccgtgaaggt gtccggcaaa gcggccaca gcggcagcac cttcagatgc tgccacgggg    6060
aggactgcag ccagatcgga ctgcatgccg cagcacccca cctggacaaa gtgaacggca    6120
tcagcgagat cgagaactcc aaggtgtacg acgatggcgc ccctcagtgc ggcatcaagt    6180
gttggttcgt gaagtccggc gagtggatca gcggcatctt ctccggcaac tggatcgtgc    6240
tgattgtgct gtgcgtgttc ctgctgtttta gcctggtgct gctgagcatt ctgtgtcccg    6300
tgcgcaagca caagaaaagc tgatgaagat ctacgtatga tcagcctcga ctgtgccttc    6360
tagttgccag ccatctgttg tttgcccctc ccccgtgcct tccttgaccc tggaaggtgc    6420
cactcccact gtccttttcct aataaaatga ggaaattgca tcgcattgtc tgagtaggtg    6480
tcattctatt ctgggggtg gggtgggca ggacagcaag ggggaggatt gggaagacaa    6540
tagcaggcat gctggggatg cggtgggctc tatggcttct gaggcggaaa gaaccagctg    6600
gggctcgaca gctcgactct agaattgctt cctcgctcac tgactcgctg cgctcggtcg    6660
ttcggctgcg gcgagcggta tcagctcact caaaggcggt aatacggtta tccacagaat    6720
caggggataa cgcaggaaag aacatgtgag caaaaggcca gcaaaaggcc aggaaccgta    6780
aaaaggccgc gttgctggcg ttttttccata ggctccgccc ccctgacgag catcacaaaa    6840
atcgacgctc aagtcagagg tggcgaaacc cgacaggact ataaagatac caggcgtttc    6900
cccctggaag ctccctcgtg cgctctcctg ttccgaccct gccgcttacc ggatacctgt    6960
ccgcctttct cccttcggga agcgtggcgc tttctcatag ctcacgctgt aggtatctca    7020
gttcggtgta ggtcgttcgc tccaagctgg gctgtgtgca cgaacccccc gttcagcccg    7080
accgctgcgc cttatccggt aactatcgtc ttgagtccaa cccggtaaga cacgacttat    7140
cgccactggc agcagccact ggtaacagga ttagcagagc gaggtatgta ggcggtgcta    7200
cagagttctt gaagtggtgg cctaactacg gctacactag aagaacagta tttggtatct    7260
gcgctctgct gaagccagtt accttcggaa aaagagttgg tagctcttga tccggcaaac    7320
aaaccaccgc tggtagcggt ggtttttttg tttgcaagca gcagattacg cgcagaaaaa    7380
aaggatctca agaagatcct ttgatctttt ctacggggtc tgacgctcag tggaacgaaa    7440
actcacgtta agggattttg gtcatgagat tatcaaaaag gatcttcacc tagatccttt    7500
taaattaaaa atgaagtttt aaatcaatct aaagtatata tgagtaaact tggtctgaca    7560
gttaccaatg cttaatcagt gaggcaccta tctcagcgat ctgtctattt cgttcatcca    7620
tagttgcctg actc                                                     7634
```

```
<210> SEQ ID NO 2
<211> LENGTH: 3411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgggcatct ggaagtggct ggtcatggct agcctcgtgt ggcccgtgct gaccctgcgg      60
aacgtgtacg acatgaagat cgagtgcccc cacaccgtgt ccttcggcga aacagcgtg     120 atcggctacg tggaactgcc ccccgtgccc ctggccgata cagctcagat ggtgcccgag    180
agcagctgca gcatggacaa ccaccagagc ctgaacacca tcaccaagta cacccaggtg    240
tcctggcggg gcaaggccga tcagagccag agcagccaga acagcttcga cagtgtgtct    300
accgaggtgg acctgaaggg cacctgtgcc ctgaagcaca gatggtgga agagagctac     360 cggtccagaa agagcgtgac ctgctacgac ctgagctgca acagcaccta ctgcaagccc    420
accctgtaca tgatcgtgcc catccacgcc tgcaacatga tgaagtcctg cctgatcgcc    480
ctgggcccct acagagtgca ggtcgtgtac gagcggagct actgcatgac cggcgtgctg    540
atcgagggca agtgcttcgt gcccgaccag agcgtggtgt ccatcatcaa gcacggcatc    600
ttcgatatcg ccagcgtgca catcgtgtgc ttttcgtgg ccgtcaaggg caacacctac     660
aagattttcg agcaggtcaa aaagagcttc gagagcacct gtaacgacac cgagaacaag    720
gtgcagggct actacatctg catcgtgggc ggcaacagcg cccccatcta cgtgcccacc    780
ctggacgact ccggtccat ggaagccttc accggcatct tcagaagccc ccacggcgag     840
gaccacgacc tggccggcga ggaaatcgcc agctactcca tcgtgggccc tgccaacgcc    900
aaggtgccac acagcgccag cagcgacacc ctgtccctga tcgcctacag cggcatcccc    960
agctacagca gcctgagcat cctgaccagc agcaccgagg ccaagcacgt gttcagccct   1020
ggcctgttcc ccaagctgaa ccacaccaac tgcgacaaga gcgccatccc cctgatctgg   1080
accggcatga tcgacctgcc cggctactac gaggccgtgc accctgcac cgtgttctgc    1140 gtgctgtctg gcctggagc cagctgcgag gccttttctg agggcggcat ctttaacatc   1200
accagcccca tgtgcctggt gtccaagcag aaccggttcc ggctgaccga gcagcaggtc   1260
aacttcgtgt gccagcgggt ggacatggac atcgtggtgt actgcaacgg ccagcggaaa   1320
gtgatcctga ccaagaccct cgtgatcggc cagtgcatct acaccatcac aagcctgttc   1380
agcctgctgc ccggcgtggc ccactctatc gccgtggaac tgtgcgtgcc cggctttcac   1440
ggctgggcca cagctgccct gctggtcacc ttctgcttcg ctgggtgct gatccccgcc    1500 atcaccttca tcatcctgac cgtgctgaag tttatcgcca acatcttcca ccaccagcaac   1560 caggaaaacc ggctcaagtc cgtgctgcgg aagatcaaag aggaattcga aaagaccaag   1620
ggcagcatgg tctgcgacgt gtgcaaatac gagtgcgaga catacaaaga gctgaaggcc   1680
cacggcgtgt cctgccctca gagccagtgc ccctactgct caccactg cgagcctacc     1740 gaggccgcct ccaggcccca ctacaaagtg tgccaggtca caccggtt cagggacgac    1800 ctgaagaaaa ccgtgacccc ccagaacttc acccccggct gctaccggac cctgaacctg   1860
ttccggtaca agagccggtg ctacatcttt accatgtgga tcttctgct ggtgctcgag    1920 tccatcctgt gggccgccag cgccagcgaa acccctctga ccccgtgtg aacgacaac    1980 gcccatggcg tgggctctgt gccatgcac accgacctgg aactggactt cagcctgacc   2040
agctccagca agtacaccta ccggcggaag ctgaccaacc ccctggaaga ggcccagagc   2100
```

| | |
|---|---|
| atcgacctgc acatcgagat cgaggaacag accatcggag tcgatgtcca cgccctggga | 2160 |
| cattggttcg acggacggct gaacctgaaa accagcttcc actgctacgg cgcctgcact | 2220 |
| aagtacgagt accectggca caccgccaag tgccactacg agcgggacta ccagtacgag | 2280 |
| acaagctggg gctgtaaccc cagcgactgt ccaggcgtgg gcaccggctg tacagcttgt | 2340 |
| ggcctgtacc tggaccagct gaagcccgtg ggctccgcct acaagatcat caccatccgg | 2400 |
| tacagcagac gcgtgtgcgt gcagttcggc gaagagaacc tgtgcaagat catcgacatg | 2460 |
| aacgactgct tcgtgtcccg gcacgtgaaa gtgtgcatca tcggcaccgt gtccaagttc | 2520 |
| agccagggcg ataccctgct gttcttcggc cctctggaag gcggcggact gatcttcaag | 2580 |
| cactggtgca caagcacctg tcagtttggc gaccccggcg acatcatgag ccccagagac | 2640 |
| aagggcttcc tgtgccccga gttccccggc agcttccgga agaagtgcaa cttcgccacc | 2700 |
| accccccatct gcgagtacga cggcaacatg gtgtccggct acaagaaagt gatggccacc | 2760 |
| atcgacagct tccagagctt caacacctcc accatgcact tcaccgacga gcggatcgag | 2820 |
| tggaaggacc ccgacggcat gctgcgggac acatcaaca tcctggtcac caaggacatc | 2880 |
| gacttcgaca acctgggcga gaaccccctg aagatcggcc tgcagacctc cagcatcgag | 2940 |
| ggcgcttggg gcagcggcgt gggctttacc ctgacctgtc tggtgtccct gaccgagtgc | 3000 |
| cccaccttcc tgacctccat caaggcctgc gacaaggcca tctgttacgg cgccgagtcc | 3060 |
| gtgaccctga agagggcca gaacaccgtg aaggtgtccg gcaaaggcgg ccacagcggc | 3120 |
| agcaccttca gatgctgcca cggggaggac tgcagccaga tcggactgca tgccgcagca | 3180 |
| ccccacctgg acaaagtgaa cggcatcagc gagatcgaga ctccaaggt gtacgacgat | 3240 |
| ggcgcccctc agtgcggcat caagtgttgg ttcgtgaagt ccggcgagtg gatcagcggc | 3300 |
| atcttctccg gcaactggat cgtgctgatt gtgctgtgcg tgttcctgct gtttagcctg | 3360 |
| gtgctgctga gcattctgtg tcccgtgcgc aagcacaaga aaagctgatg a | 3411 |

<210> SEQ ID NO 3
<211> LENGTH: 4223
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| gggggggggg ggcgctgagg tctgcctcgt gaagaaggtg ttgctgactc ataccaggcc | 60 |
| tgaatcgccc catcatccag ccagaaagtg agggagccac ggttgatgag agctttgttg | 120 |
| taggtggacc agttggtgat tttgaacttt tgctttgcca cggaacggtc tgcgttgtcg | 180 |
| ggaagatgcg tgatctgatc cttcaactca gcaaaagttc gatttattca acaaagccgc | 240 |
| cgtcccgtca gtcagcgta atgctctgcc agtgttacaa ccaattaacc aattctgatt | 300 |
| agaaaaactc atcgagcatc aaatgaaact gcaatttatt catatcagga ttatcaatac | 360 |
| catattttg aaaaagccgt ttctgtaatg aaggagaaaa ctcaccgagg cagttccata | 420 |
| ggatggcaag atcctggtat cggtctgcga ttccgactcg tccaacatca atacaaccta | 480 |
| ttaatttccc ctcgtcaaaa ataaggttat caagtgagaa atcaccatga gtgacgactg | 540 |
| aatccggtga gaatggcaaa agcttatgca tttctttcca gacttgttca acaggccagc | 600 |
| cattacgctc gtcatcaaaa tcactcgcat caaccaaacc gttattcatt cgtgattgcg | 660 |
| cctgagcgag acgaaatacg cgatcgctgt taaaaggaca attacaaaca ggaatcgaat | 720 |

```
gcaaccggcg caggaacact gccagcgcat caacaatatt ttcacctgaa tcaggatatt    780
cttctaatac ctggaatgct gttttcccgg ggatcgcagt ggtgagtaac catgcatcat    840
caggagtacg ataaaatgc ttgatggtcg gaagaggcat aaattccgtc agccagttta    900
gtctgaccat ctcatctgta acatcattgg caacgctacc tttgccatgt ttcagaaaca    960
actctggcgc atcgggcttc ccatacaatc gatagattgt cgcacctgat tgcccgacat   1020
tatcgcgagc ccatttatac ccatataaat cagcatccat gttggaattt aatcgcggcc   1080
tcgagcaaga cgtttcccgt tgaatatggc tcataacacc ccttgtatta ctgtttatgt   1140
aagcagacag ttttattgtt catgatgata tattttatc ttgtgcaatg taacatcaga    1200
gattttgaga cacaacgtgg ctttccccc ccccccggca tgcctgcagg tcgacaatat    1260
tggctattgg ccattgcata cgttgtatct atatcataat atgtacattt atattggctc   1320
atgtccaata tgaccgccat gttgacattg attattgact agttattaat agtaatcaat   1380
tacggggtca ttagttcata gcccatatat ggagttccgc gttacataac ttacggtaaa   1440
tggcccgcct ggctgaccgc ccaacgaccc ccgcccattg acgtcaataa tgacgtatgt   1500
tcccatagta acgccaatag ggactttcca ttgacgtcaa tgggtggagt atttacggta   1560
aactgcccac ttggcagtac atcaagtgta tcatatgcca agtccgcccc ctattgacgt   1620
caatgacggt aaatggcccg cctggcatta tgcccagtac atgaccttac gggactttcc   1680
tacttggcag tacatctacg tattagtcat cgctattacc atggtgatgc ggttttggca   1740
gtacaccaat gggcgtggat agcggtttga ctcacgggga tttccaagtc tccaccccat   1800
tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
ccatagaaga caccgggacc gatccagcct ccgcggccgg gaacggtgca ttggaacgcg   2040
gattccccgt gccaagagtg acgtaagtac cgcctataga ctctataggc acacccctt   2100 ggctcttatg catgctatac tgttttggc ttggggccta tacaccccg cttccttatg    2160 ctataggtga tggtatagct tagcctatag gtgtgggtta ttgaccatta ttgaccactc   2220
ccctattggt gacgatactt tccattacta atccataaca tggctctttg ccacaactat   2280
ctctattggc tatatgccaa tactctgtcc ttcagagact gacacggact ctgtattttt   2340
acaggatggg gtcccattta ttatttacaa attcacatat acaacaacgc cgtcccccgt   2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
tctgaaaatg agctcggaga ttgggctcgc accgctgacg cagatggaag acttaaggca   2700
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg ccaccagatc tacgtatgat cagcctcgac   2940
tgtgccttct agttgccagc catctgttgt ttgcccctcc ccgtgccttc ccttgaccct   3000
ggaaggtgcc actcccactg tccttttccta ataaaatgag gaaattgcat cgcattgtct   3060
gagtaggtgt cattctattc tggggggtgg ggtggggcag gacagcaagg gggaggattg   3120
```

-continued

```
ggaagacaat agcaggcatg ctggggatgc ggtgggctct atggcttctg aggcggaaag    3180
aaccagctgg ggctcgacag ctcgactcta gaattgcttc ctcgctcact gactcgctgc    3240
gctcggtcgt tcggctgcgg cgagcggtat cagctcactc aaaggcggta atacggttat    3300
ccacagaatc aggggataac gcaggaaaga acatgtgagc aaaaggccag caaaaggcca    3360
ggaaccgtaa aaaggccgcg ttgctggcgt ttttccatag gctccgcccc cctgacgagc    3420
atcacaaaaa tcgacgctca agtcagaggt ggcgaaaccc gacaggacta taaagatacc    3480
aggcgtttcc ccctggaagc tccctcgtgc gctctcctgt tccgaccctg ccgcttaccg    3540
gatacctgtc cgcctttctc ccttcgggaa gcgtggcgct ttctcatagc tcacgctgta    3600
ggtatctcag ttcggtgtag gtcgttcgct ccaagctggg ctgtgtgcac gaaccccccg    3660
ttcagcccga ccgctgcgcc ttatccggta actatcgtct tgagtccaac ccggtaagac    3720
acgacttatc gccactggca gcagccactg gtaacaggat tagcagagcg aggtatgtag    3780
gcggtgctac agagttcttg aagtggtggc ctaactacgg ctacactaga agaacagtat    3840
ttggtatctg cgctctgctg aagccagtta ccttcggaaa aagagttggt agctcttgat    3900
ccggcaaaca aaccaccgct ggtagcggtg ttttttttgt ttgcaagcag cagattacgc    3960
gcagaaaaaa aggatctcaa gaagatcctt tgatcttttc tacggggtct gacgctcagt    4020
ggaacgaaaa ctcacgttaa gggattttgg tcatgagatt atcaaaaagg atcttcacct    4080
agatcctttt aaattaaaaa tgaagtttta aatcaatcta agtatatat gagtaaactt     4140 ggtctgacag ttaccaatgc ttaatcagtg aggcacctat ctcagcgatc tgtctatttc    4200
gttcatccat agttgcctga ctc                                            4223
```

```
<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 agatct                                                                  6

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 gcggccgc                                                                8
```